United States Patent
Tahara et al.

(10) Patent No.: US 9,226,934 B2
(45) Date of Patent: Jan. 5, 2016

(54) ANTI-CANCER DRUG

(75) Inventors: Hideaki Tahara, Bunkyo-ku (JP); Masahisa Jinushi, Bunkyo-ku (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 536 days.

(21) Appl. No.: 12/995,942

(22) PCT Filed: Apr. 28, 2009

(86) PCT No.: PCT/JP2009/001940
§ 371 (c)(1),
(2), (4) Date: Dec. 2, 2010

(87) PCT Pub. No.: WO2009/147781
PCT Pub. Date: Dec. 10, 2009

(65) Prior Publication Data
US 2011/0081356 A1 Apr. 7, 2011

Related U.S. Application Data
(60) Provisional application No. 61/153,113, filed on Feb. 17, 2009.

(30) Foreign Application Priority Data
Jun. 2, 2008 (WO) .................. PCT/JP2008/001393

(51) Int. Cl.
| | |
|---|---|
| A61K 39/395 | (2006.01) |
| C07K 16/00 | (2006.01) |
| A61K 31/7068 | (2006.01) |
| A61K 31/337 | (2006.01) |
| A61K 31/4164 | (2006.01) |
| A61K 31/4745 | (2006.01) |
| A61K 31/704 | (2006.01) |
| A61K 31/7048 | (2006.01) |
| A61K 33/24 | (2006.01) |
| A61K 45/06 | (2006.01) |
| C07K 16/18 | (2006.01) |
| C07K 16/30 | (2006.01) |
| A61K 39/00 | (2006.01) |

(52) U.S. Cl.
CPC .......... *A61K 31/7068* (2013.01); *A61K 31/337* (2013.01); *A61K 31/4164* (2013.01); *A61K 31/4745* (2013.01); *A61K 31/704* (2013.01); *A61K 31/7048* (2013.01); *A61K 33/24* (2013.01); *A61K 39/395* (2013.01); *A61K 39/39558* (2013.01); *A61K 45/06* (2013.01); *C07K 16/18* (2013.01); *C07K 16/30* (2013.01); *A61K 2039/507* (2013.01); *C07K 2316/96* (2013.01); *C07K 2317/73* (2013.01)

(58) Field of Classification Search
USPC ................ 424/158.1, 130.1; 530/387.1
See application file for complete search history.

(56) References Cited

U.S. PATENT DOCUMENTS

| | | | | |
|---|---|---|---|---|
| 5,972,337 | A | * 10/1999 | Ceriani et al. | ............. 424/185.1 |
| 6,506,881 | B1 | * 1/2003 | Adair et al. | ................ 530/387.3 |
| 2006/0003960 | A1 | 1/2006 | Polakis | |

FOREIGN PATENT DOCUMENTS

| | | | | |
|---|---|---|---|---|
| JP | 2008 503480 | | 2/2008 | |
| WO | 2008 043018 | | 4/2008 | |
| WO | WO 2008043018 | * | 4/2008 | ............. A61K 39/00 |

OTHER PUBLICATIONS

Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Gura (Science, 1997, 278:1041-1042).*
NCBI MFG-E8.*
Wiesenthal, (Human Tumor Assay Journal, on-line at (http://weisenthal.org/synergy1.htm, Mar. 14, 2012).*
Berenbaum (Clin exp Immunol, 1997, 28:1-18).*
Stubbs, J.D., et al., "cDNA cloning of a mouse mammary epithelial cell surface protein reveals the existence of epidermal growth factor-like domains linked to factor VIII-like sequences," Proc. Natl. Acad. Sci. USA, vol. 87, pp. 8417-8421, (Nov. 1990).
Hanayama, R., et al., "Identification of a factor that links apoptotic cells to phagocytes," Nature, vol. 417, pp. 182-187, (May 9, 2002).
Hanayama, R., et al., "Autoimmune Disease and Impaired Uptake of Apoptotic Cells in MFG-E8-Deficient Mice," Science, vol. 304, pp. 1147-1150, (May 21, 2004).
Jinushi, M. et al., "MFG-E8-mediated uptake of apoptotic cells by APCs links the pro- and antiinflammatory activities of GM-CSF," The Journal of Clinical Investigation, vol. 117, No. 7, pp. 1902-1913, (Jul. 2007).
Carmon, L., et al., "Characterization of novel breast carcinoma-associated BA46-derived peptides in HLA-A2.1/D$^b$-β2m transgenic mice," The Journal of Clinical Investigation, vol. 110, No. 4, pp. 453-462, (Aug. 2002).
Neutzner, M., et al., "MFG-E8/Lactadherin Promotes Tumor Growth in an Angiogenesis-Dependent Transgenic Mouse Model of Multi-stage Carcinogenesis," Cancer Res., vol. 67, No. 14, pp. 6777-6785, (Jul. 15, 2007).
International Search Report issued May 26, 2009 in PCT/JP09/001940 filed Apr. 28, 2009.

(Continued)

*Primary Examiner* — Yan Xiao
(74) *Attorney, Agent, or Firm* — Oblon, McClelland, Maier & Neustadt, L.L.P.

(57) ABSTRACT

The present invention is directed to an anti-cancer drug containing an anti-MFG-E8 antibody as an active ingredient, and to an anti-cancer drug which employs an anti-MFG-E8 antibody in combination with a cancer therapy employing an anti-cancer agent other than the anti-MFG-E8 antibody.

9 Claims, 24 Drawing Sheets

(56) References Cited

OTHER PUBLICATIONS

Extended European Search Report issued Aug. 23, 2012 in Patent Application No. 09758048.4.

Joseph R. Couto, et al. "Anti-BA46 Monoclonal Antibody Mc3: Humanization Using a Novel Positional Consensus and in Vivo and in Vitro Characterization", Cancer Research, vol. 55, No. 8, XP000919432, Apr. 15, 1995, pp. 1717-1722.

David Larocca, et al., "A MR 46,000 Human Milk Fat Globule Protein That is Highly Expressed in Human Breast Tumors Contains Factor VIII-Like Domains", Cancer Research, vol. 51, XP000431678 Sep. 15, 1991, pp. 4994-4998.

Barry D Shur, et al., "SED1 function during mammalian sperm-egg adhesion", Current Opinion in Cell Biology, vol. 16, No. 5, XP005041768, Oct. 1, 2004, pp. 477-485.

* cited by examiner

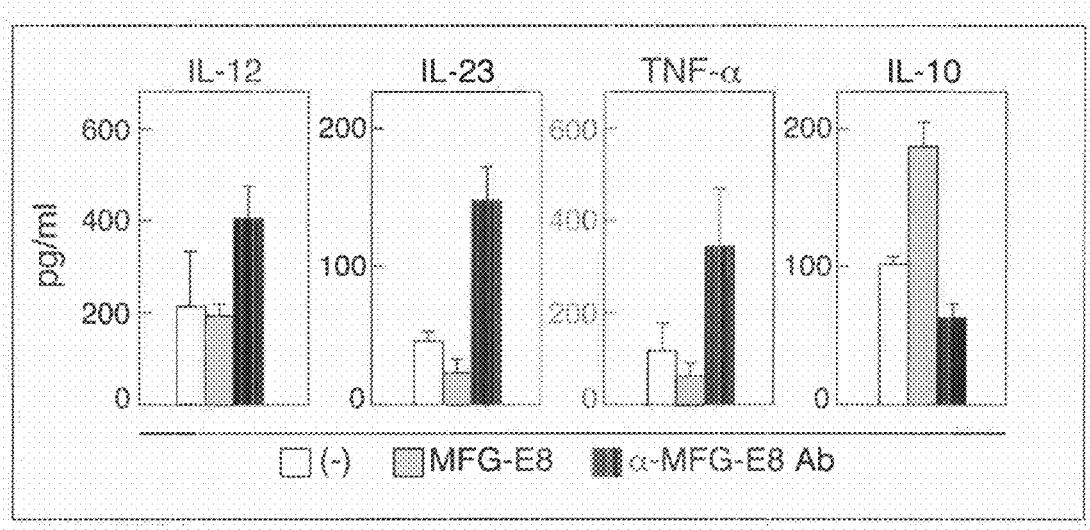

ANTI-CANCER DRUG

TECHNICAL FIELD

The present invention relates to a novel anti-cancer drug and, more particularly, to an anti-cancer drug which potentiates the therapeutic effect of a cancer therapy that does not employ this particular anti-cancer drug.

BACKGROUND ART

In 1981, cancer has become the leading cause of death in Japan, and has remained the leading cause of death since then. Thus, there is continuous demand for novel cancer therapy. Currently employed cancer therapies include surgical therapy, radiotherapy, and chemotherapy (by means of anti-cancer agents). Even after surgical operation, a cancer therapy by an anti-cancer agent is also employed.

Examples of anti-cancer agents currently employed include an alkylating agent, a metabolic antagonist, an alkaloid anti-cancer agent, an antibiotic anti-cancer agent, and a platinum drug. However, the therapeutic effects of the anti-cancer agents are not sufficient at present, and adverse side effects often arise, which are problematic. From this viewpoint, development of a more improved anti-cancer agent is envisaged.

Meanwhile, MFG-E8 (a milk fat globule membrane glycoprotein: milk fat globule-EGF factor 8) was previously identified as a factor which is secreted through the mammary gland and which promotes differentiation of the mammary gland and suckling stimulation (Non-Patent Document 1). In recent years, in addition to the above actions, MFG-E8 has been found to have a variety of functions. Among them, one important function thereof is that MFG-E8 serves as an opsonin which recognizes phosphatidylserine present on the surfaces of apoptotic cells, to thereby promote the phagocytic activity of macrophages and dendritic cells, whereby immune tolerance is maintained (Non-Patent Documents 2, 3). Furthermore, MFG-E8 is known to promote growth of Foxp 3-positive-regulatory T cells, to thereby induce tolerance, whereby the antitumor immunity of an anti-tumor vaccine is negatively controlled (Non-Patent Document 4). On the basis of these findings, a therapeutic method employing a decoy gene of MFG-E8 and an anti-MFG-E8 antibody were previously developed with the aim of combined use with a tumor antigen such as a cancer vaccine, and a patent application was filed (Patent Document 1). Also, studies revealed that MFG-E8 is widely expressed not only in antigen-presenting cells such as dendritic cells but also in cells of a tumor (e.g., breast cancer, colon carcinoma, or melanoma) (Non-Patent Document 5), and that MFG-E8 has a tumor-activating action through promoting angiogenesis and tumor metastasis and positively correlates with the clinical progress of melanoma (Non-Patent Document 6).

PRIOR ART DOCUMENTS

Patent Document

Patent Document 1: WO 2008/043018

Non-Patent Documents

Non-Patent Document 1: Stubbs T et al., 1990. cDNA reveals the existence sequences. Proc. Natl. Acad. Sci. USA 87: 8417-8421

Non-Patent Document 2: Hanayama R. et al., 2002. Nature 417: 182-187

Non-Patent Document 3: Hanayama R., et al., 2004. Autoimmune MFG-E8-deficient mice. Science 304: 1147-1150

Non-Patent Document 4: Jinushi M., et al., 2007. MFG-E8 mediated uptake of apoptotic cells by APCs links the pro- and anti-inflammatory activities of GM-CSF. J. Clin. Invest. 117: 1902-1913

Non-Patent Document 5: Carmon L., et al., 2002. Characterization of novel breast carcinoma-associated BA46-derived peptides in HLA-2.1/D(b)-beta2m transgenic mice. J. Clin. Invest. 110: 453-462.

Non-Patent Document 6: Neutzner M., et al., 2007. MFG-E8/lactadherin promotes tumor growth in an angiogenesis-dependent transgenic mouse model of multistage carcinogenesis. Cancer Res. 67: 6777-6785

SUMMARY OF THE INVENTION

Problems to be Solved by the Invention

An object of the present invention is to provide a novel anti-cancer drug and a novel cancer therapeutic method.

Means for Solving the Problems

The present inventors have carried out extensive studies on pharmacological actions of anti-MFG-E8 antibodies, and have found that anti-MFG-E8 antibody alone exhibits excellent anti-cancer effect. The inventors have conducted further studies and, as a result, have also found that, even though no tumor antigen is administered to a patient, the anti-MFG-E8 antibody exhibits remarkably potent anti-cancer effect through combination with a cancer therapy employing an anti-cancer agent other than the anti-MFG-E8 antibody, as compared with the anti-cancer effect of the anti-MFG-E8 antibody alone, whereby the antibody particularly effectively potentiates the effect of a cancer therapy that does not employ the antibody. The inventors have also found that the anti-MFG-E8 antibody activates intra-tumoral and systemic anti-tumor immune responses, to thereby cause and promote anti-tumor immune reactions including induction of tumor-specific cytotoxic T cells. The inventors have also found that, particularly, the anti-MFG-E8 antibody, which itself can cause anti-tumor immune responses, serves as a useful drug for the induction of potent and specific immune responses, when the antibody is used in combination with a drug or therapy which is toxic to the target cell. The inventors have also found that this specific immune response induction provided by the anti-MFG-E8 antibody is established through switching of a system via $\alpha_v\beta_3$ integrin to a system via an Fc receptor, that both systems present on the surfaces of antigen-presenting cells including dendritic cells. As used herein, the term "specific immune" refers to the antigen-specific humoral and cellular immunity provided by B cells or the like and T cells or the like, respectively.

Accordingly, the present invention provides an anti-cancer drug containing an anti-MFG-E8 antibody as an active ingredient.

The present invention also provides an anti-cancer drug containing an anti-MFG-E8 antibody and an anti-cancer agent other than the antibody.

The present invention also provides an anti-cancer drug containing an anti-MFG-E8 antibody, for use in combination with a cancer therapy that does not employ the anti-MFG-E8 antibody. A characteristic feature of the aforementioned anti-cancer drug resides in that the anti-cancer drug has a tumorcell-specific anti-cancer action even in the absence of a tumor antigen or tumor cells. One possible action mechanism thereof is that the anti-MFG-E8 antibody serving as an active ingredient promotes, by the mediation of an Fc-receptor, intake of tumor cells in an apoptosis state assisted by antigen-presenting cells present in the body, to thereby induce specific anti-tumor immunity mainly based on cytotoxic T cells.

The present invention also provides a drug for the induction of target-cell-specific immune responses, which drug contains an anti-MFG-E8 antibody as an active ingredient and is used in combination with a drug or therapy which is toxic to the target cell. The target cell is preferably a tumor cell, and the anti-MFG-E8 antibody is characterized by inducing specific immunity against the target cell by the mediation of an Fc-receptor present on the surfaces of antigen-presenting cells. In one embodiment of the present invention, there is provided an immune pathway switching agent containing an anti-MFG-E8 antibody, wherein the anti-MFG-E8 antibody suppresses tolerance to a target cell in which expression of MFG-E8 has been induced by a drug or therapy which is toxic to the target cell, and the anti-MFG-E8 antibody promotes, by the mediation of an Fc-receptor, uptake of target cells in an apoptosis state assisted by antigen-presenting cells present in the body, to thereby potentiate anti-tumor immunity mainly based on cytotoxic T cells.

The present invention also provides use of an anti-MFG-E8 antibody for producing an anti-cancer drug.

The present invention also provides use of an anti-MFG-E8 antibody for producing an anti-cancer drug containing, in combination, the anti-MFG-E8 antibody and an anti-cancer agent other than the antibody.

The present invention also provides use of an anti-MFG-E8 antibody for producing an anti-cancer drug for use in combination with a cancer therapy that does not employ this particular antibody.

The present invention also provides use of an anti-MFG-E8 antibody for producing a drug for the induction of target-cell-specific immune responses, for use in combination with a drug or therapy which is toxic to the target cell.

The present invention also provides a method of the treatment of cancer, characterized by administering an anti-MFG-E8 antibody to a patient in need thereof.

The present invention also provides a method of the treatment of cancer, characterized by administering, to a patient in need thereof, an anti-MFG-E8 antibody and an anti-cancer agent other than the antibody, in combination.

The present invention also provides a method of the treatment of cancer, characterized by comprising employing, in combination, administration of an anti-MFG-E8 antibody to a patient in need thereof, and a cancer therapy that does not employ the anti-MFG-E8 antibody.

The present invention also provides a specific immune response induction method, characterized by employing an anti-MFG-E8 antibody and a drug or therapy which is toxic to the target cell, in combination.

Effects of the Invention

Through combination of the anti-MFG-E8 antibody employed in the present invention and a cancer therapy that does not employ the anti-MFG-E8 antibody (e.g., an anti-cancer agent other than the anti-MFG-E8 antibody), the anti-cancer effect can be drastically enhanced, whereby a more improved cancer therapeutic effect can be attained. In addition, when the anti-MFG-E8 antibody is employed in combination with an anti-cancer agent other than the anti-MFG-E8 antibody or a cancer therapy (e.g., radiotherapy), which per se provides a patient with adverse side effects, the dose of the anti-cancer agent or the intensity of the cancer therapy (radiation dose in radiotherapy) can be reduced, and the intervals of administration of the anti-cancer agent or the duration of the cancer therapy can be prolonged. Thus, the adverse side effects can be mitigated. When the occurrence of the side effects is minimized, a therapy employing the anti-cancer agent, radiotherapy, etc. can be continuously performed for a prolonged period of time, leading to further enhancement in cancer therapeutic effect.

In the present invention, the cancer therapeutic effect provided by the anti-MFG-E8 antibody is attained through employment of a tumor-cell-derived antigen present in a cancer patient, to thereby induce specific immunity. Therefore, according to the present invention, a target therapeutic effect can be attained without separating a tumor-cell-antigen such as a conventional tumor vaccine from a patient or identifying the antigen, or administering a tumor antigen to a patient during the cancer therapy.

In the present invention, the specific immune response induction action of the anti-MFG-E8 antibody has been found to be realized by suppressing a tolerance pathway by the mediation of $\alpha_v\beta_3$ integrin present on the surfaces of antigen-presenting cells such as dendritic cells and macrophages, to thereby switch the pathway to an immunity potentiating pathway via an Fc receptor.

BRIEF DESCRIPTION OF THE DRAWINGS

[FIG. 24] Graphs showing the effects of anti-MFG-E8 antibody on production of cytokines (IL-12, IL-23, TNF-α, and IL-10) by antigen-presenting cells.

MODES FOR CARRYING OUT THE INVENTIONS

Figure 1:
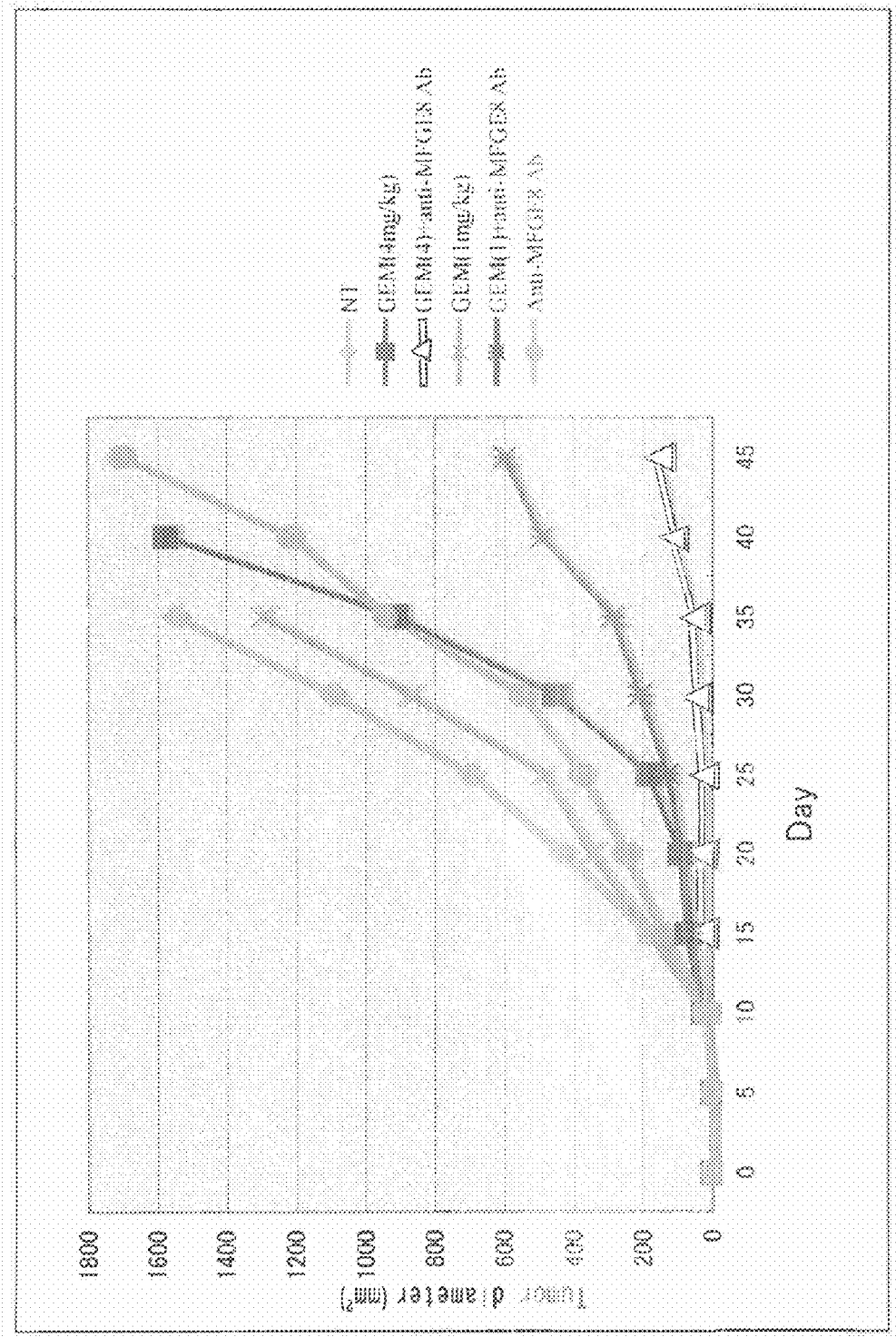
[FIG. 1] A graph showing anti-tumor effects observed in subcutaneous tumor models of mouse colon carcinoma cells (MC38), including the cases of administration of anti-MFG-E8 antibody alone and the cases of combined administration with anti-cancer agent (gemcitabine: GEM). NT represents a non-treatment group, and Anti-MFG-E8Ab represents anti-MFG-E8 antibody (the same applies to the following).
Figure 2:
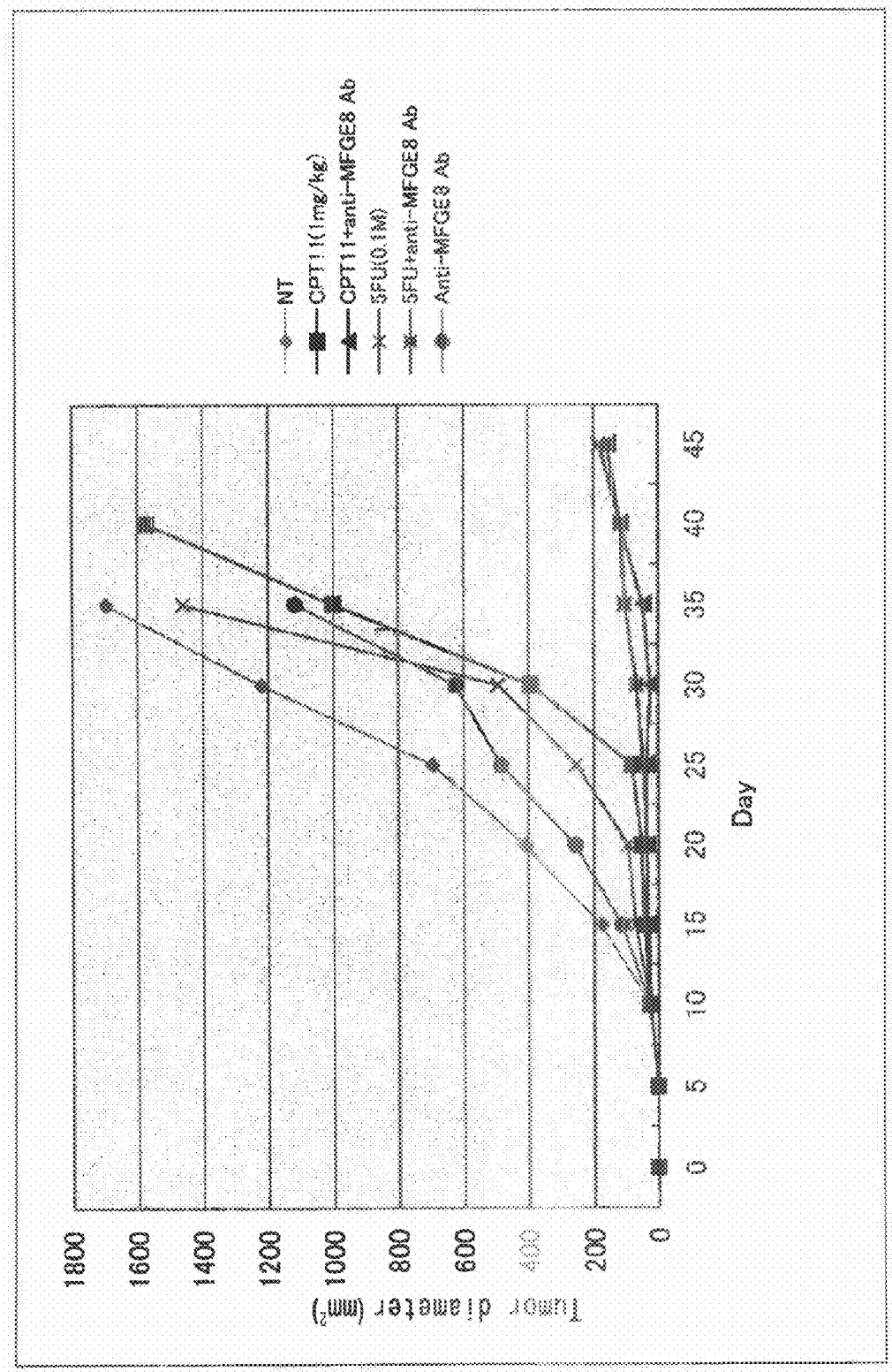
[FIG. 2] A graph showing anti-tumor effects observed in the same tumor models as shown in FIG. 1, including the cases of administration of anti-MFG-E8 antibody alone and the cases of combined administration with anti-cancer agent (CPT11 or 5FU).
Figure 3:
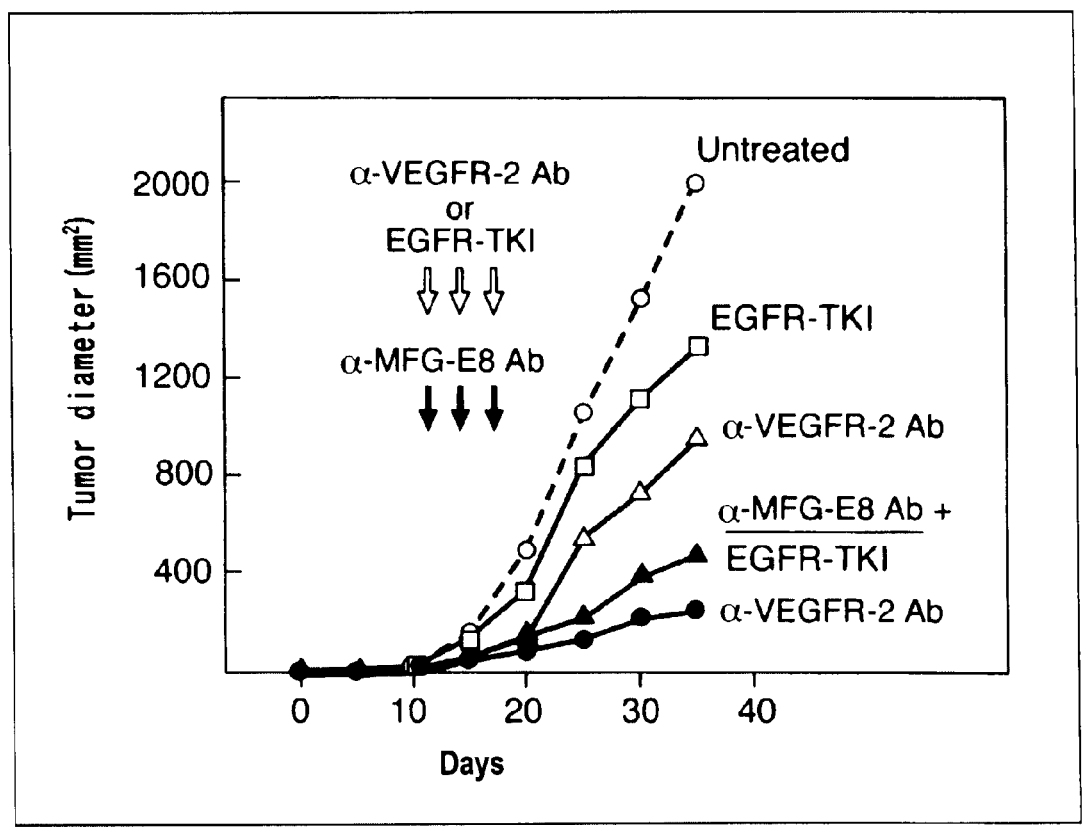
[FIG. 3] A graph showing anti-tumor effects observed in the same tumor models as shown in FIG. 1, including the cases of administration of anti-MFG-E8 antibody alone and the cases of combined administration with EGFR-TK1 or α-VEGFR-2Ab.
Figure 4:
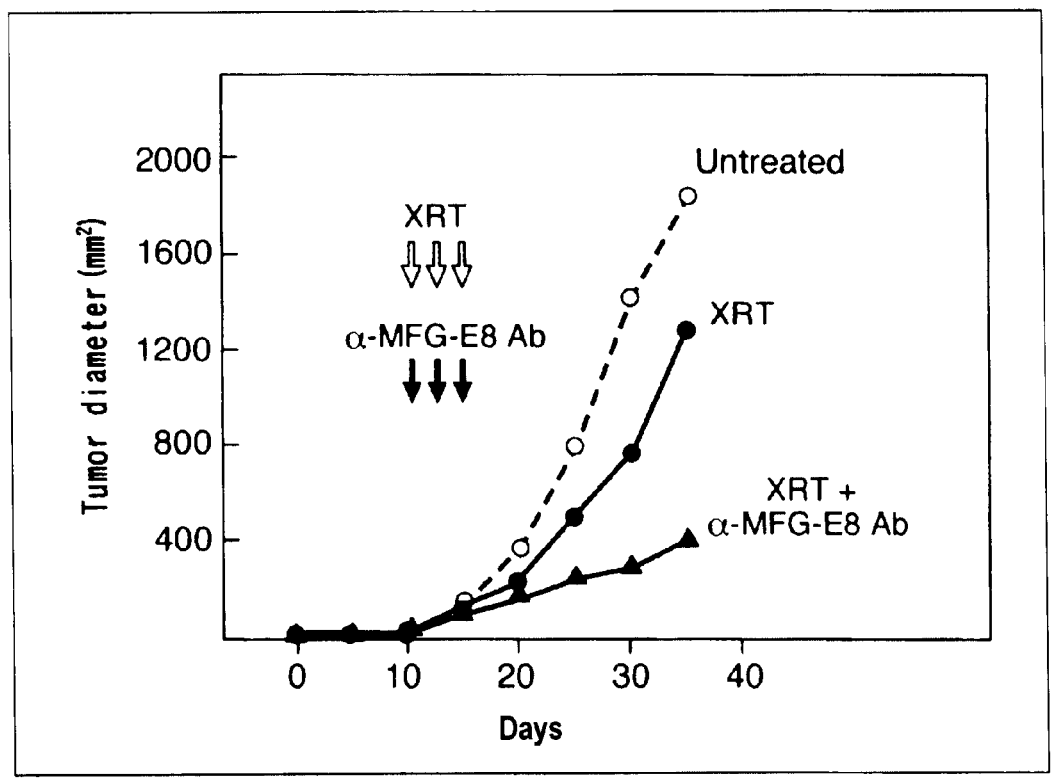
[FIG. 4] A graph showing anti-tumor effects observed in the same tumor models as shown in FIG. 1, including the cases of administration of anti-MFG-E8 antibody alone and the cases of administration of the antibody in combination with radiotherapy (XRT).
Figure 5:
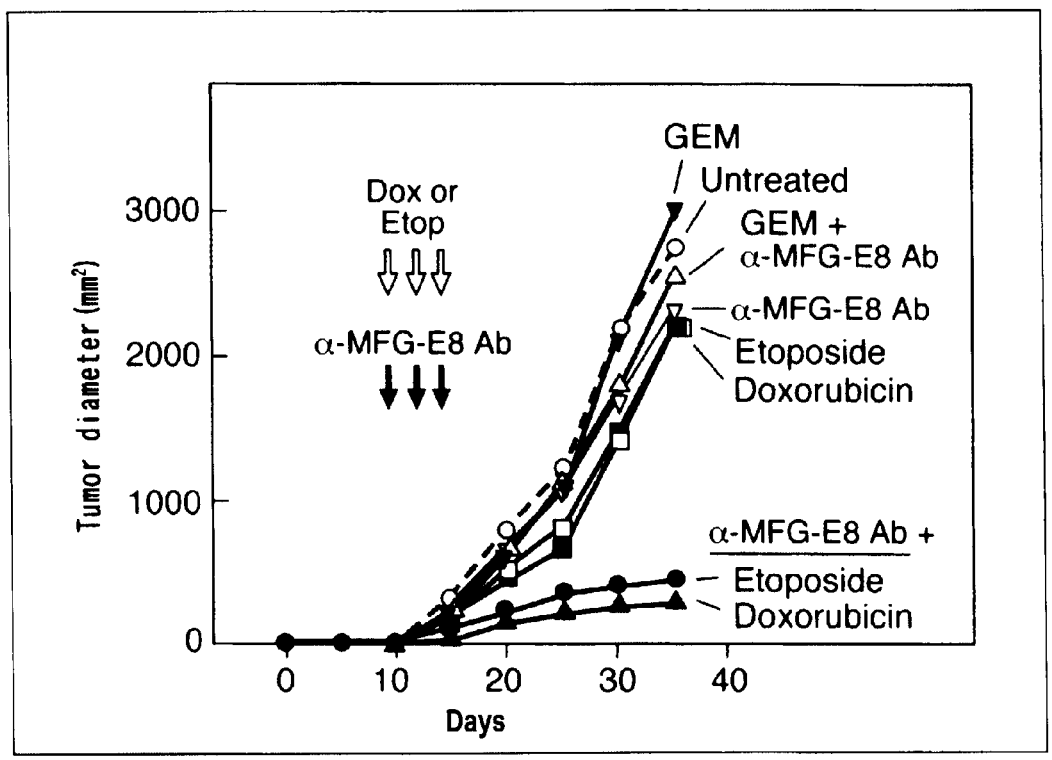
[FIG. 5] A graph showing anti-tumor effects observed in subcutaneous tumor models of mouse malignant melanoma cells (B16), including the cases of administration of anti-MFG-E8 antibody alone and the cases of combined administration with anti-cancer agent (doxorubicin (Dox) or etoposide (Etop)).

The active ingredient of the anti-cancer drug of the present invention is an anti-MFG-E8 antibody. No particular limitation is imposed on the anti-MFG-E8 antibody employed in the present invention, so long as the antibody binds specifically to MFG-E8, to thereby inhibit the function of MFG-E8.

Examples of the antibody of the present invention include monoclonal antibodies, polyclonal antibodies, antibodies maintaining specific binding performance to an antigenic determinant group, and variants and derivatives of an antibody such as T-cell receptor fragments.

No particular limitation is imposed on the type of the antibody employed in the present invention, and there may be appropriately employed a variety of antibodies such as mouse antibodies, human antibodies, rat antibodies, rabbit antibodies, sheep antibodies, camel antibodies, avian antibodies, and recombinant antibodies (i.e., intentionally modified antibodies for, for example, reducing xenoantigenicity to human) such as chimera antibodies and humanized antibodies. Such recombinant antibodies may be produced through a known method. A chimera antibody is formed of variable regions of a heavy chain and a light chain of an antibody of a mammal (non-human) such as a mouse, and constant regions of a heavy chain and a light chain of a human antibody. Such a chimera antibody may be produced by ligating a DNA fragment coding for a variable region of a mouse antibody to a DNA fragment coding for a constant region of a human antibody, introducing the ligated product into an expression vector, and introducing the vector into a host for production. The humanized antibody, which is also called a "reshaped human antibody," is formed by transplanting a complementarity-determining region (CDR) of an antibody of a mammal (non-human), such as a mouse, into a CDR of a human antibody, and a recombination technique for the humanized antibody is generally known. Specifically, a DNA sequence formed through ligating a CDR of a mouse antibody to a framework region (FR) of a human antibody is synthesized through PCR from several oligonucleotides prepared so as to have an overlapped portion at an end thereof. The thus-produced DNA fragment is ligated to a DNA fragment coding for a constant region of human antibody, and the ligated product is incorporated into an expression vector, followed by introducing the vector into a host for production (see European Patent Application Laid-Open No. EP 239,400, and International Patent Application Laid-Open No. WO 96/02576). The FR of the human antibody ligated by the mediation of CDR is selected from FRs having a complementarity-determining region which forms a suitable antigen-binding site. If needed, an amino acid of the framework region in the variable region of the antibody may be substituted, such that a complementarity-determining region of the reshaped human antibody forms an appropriate antigen-binding site (Sato, K. et al., Cancer Res., 1993, 53, 851-856).

There have also been known methods for recovering a human antibody. In one method, human lymphocytes are sensitized in vitro with an antigen of interest or a cell expressing an antigen of interest, and the thus-sensitized lymphocytes are fused with human myeloma cells (e.g., U266), whereby a human antibody of interest having binding activity to a target antigen is produced (see JP-B-1989-59878). Alternatively, a human antibody of interest may be recovered through immunizing a transgenic animals having all repertories of the human antibody gene with an antigen of interest (see WO 93/12227, WO 92/03918, WO 94/02602, WO 94/25585, WO 96/34096, and WO 96/33735). Also known is a technique for recovering a human antibody including panning by using a human antibody library. For example, a variable region of a human antibody in the form of a single-strand antibody (scFv) is expressed on the surfaces of phages through the phage display method, and a phage which binds to a target antigen can be selected. Through analysis of the gene of the selected phage, a DNA sequence coding for a variable region of the human antibody which binds to the target antigen can be determined. Once the DNA sequence of the antigen-binding scFv has been elucidated, an appropriate expression vector of the sequence can be produced, and the human antibody of interest can be recovered by using the expression vector. The method is already known (see WO 92/01047, WO 92/20791, WO 93/06213, WO 93/11236, WO 93/19172, WO 95/01438, and WO 95/15388).

So long as the aforementioned antibodies maintain a property of recognizing the entirety or a part of a protein encoded by an MFG-E8 gene, the antibodies may also be low-molecule antibodies such as antibody fragments (fragments) or modified antibodies. Specific examples of such antibody fragments include Fab, Fab', F(ab')$_2$, Fv, and Diabody. For producing such antibody fragments, a gene coding for such an antibody fragment is produced and introduced into an expression vector, and the vector is expressed in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

As a modified antibody, an antibody which has been bound to a molecule such as polyethylene glycol (PEG) may also be employed. Such a modified antibody may be produced through chemical modification of the as-produced antibody. Notably, the method of modifying antibodies has been established in the art.

In the present invention, for the purpose of, for example, potentiating cytotoxic activity, an antibody in which a sugar chain thereof has been modified may also be employed. The technique for modifying a sugar chain of an antibody is known (see, for example, WO 00/61739 and WO 02/31140).

The antibody of the present invention also includes a multi-specific antibody, having specificities to two or more different antigens. Generally, such a multi-specific antibody molecule binds to two antigens (i.e., bi-specific antibody). However, the "multi-specific antibody" employed in the present invention includes antibodies each having a specificity to two or more (e.g., 3 types of) antigens. The multi-specific antibody may be a full-length antibody or a fragment of the antibody (e.g., F(ab')$_2$ bi-specific antibody).

The methods for producing multi-specific antibodies are known in the art. Production of a full-length bi-specific antibody includes co-expression of two immunoglobulin heavy chain-light chains having different specificities (Millstein et al., Nature 305: 537-539 (1983)). Since immunoglobulin heavy chains and light chains are combined at random, a plurality of hybridomas (quadromas) prepared for co-expression are the mixture of hybridomas expressing different antibody molecules. Therefore, hybridomas producing two target bi-specific antibodies must be selected therefrom. The selection may be performed through a technique such as affinity chromatography. In an alternative method, a variable region of an antibody having a binding specificity of interest is fused with a constant domain sequence of immunoglobulin. The constant domain sequence preferably includes at least a part of a hinge domain, a CH2 domain, and a CH3 domain of the constant domain of the immunoglobulin heavy chain. More preferably, the constant domain sequence further contains a CH1 domain of the heavy chain which is essential for binding with the light chain. A DNA fragment coding for the immunoglobulin heavy chain fused product and an optional DNA fragment coding for the immunoglobulin light chain are inserted into different expression vectors, and an appropriate host is transformed. In the case where individual genes are inserted into different expression vectors, the ratio between two chains may not be 1:1, if the yield of a target antibody is enhanced at such a ratio. In this case, the expression ratio of each chain can be controlled, which is convenient. However, needless to say, a gene coding for a plurality of chains may be inserted into a single vector.

In a preferred embodiment, a bi-specific antibody has a heavy chain having a first binding property as one arm of the hybrid immunoglobulin, and a heavy chain-light chain complex having a second binding property as the other arm. When only one arm has a light chain, a bi-specific antibody can be readily separated from other immunoglobulins (see WO 94/04690). The method for producing a bi-specific antibody may also be based on the method by Suresh et al. (Methods in Enzymology 121: 210 (1986)). For decreasing homo-dimers and increasing heter-dimers contained in the final product obtained from a recombinant cell culture, there has been known a method in which a constant antibody domain of CH3 is employed; in one antibody molecule, one or more amino acids having a small side chain which are present on the surface binding to the counter molecule are changed to amino acids having a large side chain (e.g., tyrosine and tryptophan); and amino acids having a large side chain corresponding to the counter antibody molecule are changed to amino acids having a small side chain (e.g., alanine and threonine), to thereby provide a hole corresponding to the large side chain of the first antibody molecule (WO 96/27011).

The bi-specific antibody also includes, for example, a hetero-conjugated antibody in which one antibody is bound to avidin, and the other antibody is bound to biotin or the like (U.S. Pat. No. 4,676,980; WO 91/00360; WO 92/00373; and EP 03089). The cross-linking agent employed for producing such a hetero-conjugated antibody are widely known, and examples thereof are described in, for example, U.S. Pat. No. 4,676,980.

As an alternative method, there has been reported a method for producing a bi-specific antibody from antibody fragments. For example, the production may be accomplished by means of chemical bonding. In one specific process, F(ab')$_2$ fragments are produced and then reduced by use of a dithiol complexing agent (sodium arsanilate) in order to prevent formation of disulfide in the same molecule. Subsequently, the F(ab')$_2$ fragments are transformed to a thionitrobenzoate (TNB) derivative. By use of mercaptoethlamine, one F(ab')$_2$-TNB derivative is reduced again to a Fab'-thiol derivative, and an equiamount of the F(ab')$_2$-TNB derivative and the Fab'-thiol are mixed to thereby produce a bi-specific antibody of interest.

Also a variety of methods are reported in which a bi-specific antibody is produced directly from a recombinant cell culture, followed by isolation. One of such methods is production of a bi-specific antibody through employment of a leucine zipper (Kostelny et al., J. Immunol. 148(5): 1547-1553 (1992)). In this method, leucine zipper peptides of Fos protein and Jun protein are linked to different antibodies at a Fab' site through gene fusion. An antibody of homo-dimer is reduced such that a monomer is formed in a hinge domain thereof, and re-oxidized to form a hetero-dimer. Still alternatively, a heavy chain variable domain (VH) is linked to a light chain variable domain (VL) via a linker having such a short length that coupling of these two domains is inhibited, but coupling with complementary VL and VH domains is allowed, whereby two antigen-binding sites are formed (Hollinger et al., Proc. Natl. Acad. Sci. USA 90: 6444-6448 (1993)). A dimer employing a single-strand chain Fv (sFV) is also reported (Gruger et al., J. Immunol. 152: 5368 (1994)). In addition to the aforementioned bi-specific antibodies, a tri-specific antibody is also reported (Tutt et al., J. Immunol. 147: 60 (1991)).

The antibody and antibody fragment employed in the present invention may be produced by any appropriate means, for example, in vivo, cultured cells, in vitro translation reaction, or recombinant DNA expression system.

The techniques for producing monoclonal antibodies and hybridomas are well known in the art (Campbell, "Monoclonal Antibody Technology Laboratory Techniques in Biochemistry and Molecular Biology," Elsevier Science Publishers, Amsterdam, The Netherlands, 1984; St. Groth et al., J. Immunol. Methods 35: 1-21, 1980). Any animals (mouse, rabbit, etc.) which are known to form a corresponding antibody by using a protein or its fragment encoded by an MFG-E8 gene as an immunogen may be immunized through subcutaneous or intraperitoneal injection. During immunization, an adjuvant may be used. Such an adjuvant is well known in the art.

The polyclonal antibody may be produced through isolating an anti-serum containing a target antibody from an immunized animal, and selecting an antibody having a target specificity through screening based on a technique well known in the art such as ELISA assay, western blotting assay, or radioimmunoassay.

The monoclonal antibody may be produced through cutting out spleen cells from an immunized animal, and fusing the cells with myeloma cells, to thereby produce hybridoma cells producing a monoclonal antibody. Hybridoma cells producing an antibody that recognizes a target protein or its fragment are selected through screening based on a technique well known in the art such as ELISA assay, western blotting assay, or radioimmunoassay. Alternatively, the monoclonal antibody may be through cloning a hybridoma secreting an antibody of interest, cultivating the cloned hybridoma under suitable conditions, recovering a secreted antibody, and purifying the antibody through a technique well known in the art, such as ion-exchange column chromatography or affinity chromatography. Still alternatively, a human monoclonal antibody may be produced by using xeno-mouse cells (see Green, J. Immunol. Methods 231: 11-23, 1999; and Wells, Eek, Chem. Biol. 2000 August; 7(8): R185-6). Currently, production of a monoclonal antibody is performed on the basis of phage display without immunizing. The antibodies employed in the present invention may be produced through any of the aforementioned methods.

The DNA fragment coding for the monoclonal antibody may be readily isolated through a routine method (e.g., by using an oligonucleotide probe which specifically binds to genes coding for a heavy chain and a light chain of the monoclonal antibody) and sequence of the isolated DNA fragment can be determined. A preferred material for producing such a DNA fragment is a hybridoma cell. After the DNA fragment is isolated, the DNA fragment is inserted into an expression vector, and recombinant host cells are obtained by introducing the expression vector into hosts such as E. coli cells, monkey COS cells, Chinese hamster oval (CHO) cells or myeloma cells in which no immunoglobulin is produced unless the cells are transformed, and a monoclonal antibody is produced from the recombinant host cells. Still alternatively, an antibody or a fragment thereof may be isolated from an antibody phage library produced through a technique disclosed by McCafferty et al. (Nature 348: 552-554 (1990)).

No particular limitation is imposed on the anti-cancer agent which can be used in combination with the anti-MFG-E8 antibody, so long as the anti-cancer agent exhibits anti-cancer effect. A tumor-cell-toxic anti-cancer agent is particularly preferred, from the viewpoint of a synergistic effect.

Examples of the anti-cancer agent (other than anti-MFG-E8 antibody) include an alkylating agent, a metabolic antagonist, a microtubule inhibitor, an antibiotic anti-cancer agent, a topoisomerase inhibitor, a platinum drug, a molecular targeted drug, a hormone agent, and a biological drug. Examples of the alkylating agent include cyclophosphamide, ifosfamide, nitrosourea, dacarbazine, temozolomide, nimustine, busulfan, melphalan, procarbazine, and ranimustine. Examples of the metabolic antagonist include enocitabine, carmofur, capecitabine, tegafur, tegafur-uracil, tegafur-gimeracil-oteracil potassium, gemcitabine, cytarabine, cytarabine ocfosfate, nelarabine, fluorouracil, fludarabine, pemetrexed, pentostatin, methotrexate, cladribine, doxifluridine, hydroxycarbamide, and mercaptopurine. Examples of the microtubule inhibitor include an alkaloid anti-cancer agent (e.g., vincristine) and a taxan anti-cancer agent (e.g., docetaxel and paclitaxel). Examples of the antibiotic anti-cancer agent include mitomycin C, doxorubicin, epirubicin, daunorubicin, bleomycin, actinomycin D, aclarubicin, idarubicin, pirarubicin, peplomycin, mitoxantrone, amrubicin, and zinostatin stimalamer. Examples of the topoisomerase inhibitor include CPT-11, irinotecan, nogitecan (topoisomerase I inhibitors), and etoposide and sobuzoxane (topoisomerase II inhibitors). Examples of the platinum drug include cisplatin, nedaplatin, oxaliplatin, and carboplatin. Examples of the hormone agent include dexamethasone, finasteride, tamoxifen, astrozole, exemestane, ethinylestradiol, chlormadinone, goserelin, bicalutamide, flutamide, predonisolone, leuprorelin, letrozole, estramustine, toremifene, fosfestrol, mitotane, methyltestosterone, medroxyprogesterone, and mepitiostane. Examples of the biological drug include interferon α, interferon β, interferon γ, interleukin 2, ubenimex, and dry BCG. Examples of the molecular targeted drug include rituximab, alemtuzumab, trastuzumab, cetuximab, panitumumab, imatinib, dasatinib, nilotinib, gefitinib, erlotinib, temcirolimus, bevacizumab, VEGF trap, sunitinib, sorafenib, tosituzumab, bortezomib, gemutuzumab-ozogamicin, ibritumomab-ozogamicin, ibritumomab tiuxetan, tamibarotene, and tretinoin. In addition to the above specified molecular targeted drugs, there may be included the following molecular targeted drugs: angiogenesis-targeted inhibitors such as human epidermal growth factor receptor 2 inhibitor, epidermal growth factor receptor inhibitor, Bcr-Abl tyrosine kinase inhibitor, epidermal growth factor tyrosine kinase inhibitor, mTOR inhibitor, and endothelial growth factor receptor 2 inhibitor (α-VEGFR-2 antibody); tyrosine kinase inhibitors such as MAP kinase inhibitor; cytokine-targeted inhibitors, proteasome inhibitor, and antibody-anti-cancer agent formulations. These inhibitors also include corresponding antibodies. In addition to the aforementioned drugs, the following pharmaceuticals may be used in combination: thalidomide, everolimus, elplat, ABI-007, ixabepilon, miriplatin, lapatinib, pemetrexed, cladribine, liposomal doxorubicin, Z-100, hycamtin, vandetanib, ZD4054, anastrozole, GSK1572932A, pazopanib, denosmab, S-1, motesanib, trastuzumab, enzastaurin, immucyst, NIK-333, axitinib, bostinib, E7080, soblidotin, degarelix, fluvestrant, zoladex, cediranib, eribulin, TSU-68, TAC-101, TAS-108, NK911, NK105, erlotinib, LBH589, MK-0457, tamibarotene, lenalidomide, BNP1350, AZD0530, AZD1152, AZD2281, AZD4877, ABT-869, ONO-4538, OTS102, KW-0761, ARQ197, ofatumab, AMG655, TAK-700, TAK-683, TAK-448, CBP501, TAK-285, TAK-593, MLN8054, MLN4924, pertuzumab, R1507, NK012, BIBF1120, BIBW2992, Patupilone, MK-2461, CP751,871, PF-00299804, satraplatin, CMC-544, YM155, GPI21016, and YHO-13351. Among these anti-cancer agents, an alkylating agent, a metabolic antagonist, a microtubule inhibitor, an antibiotic anti-cancer agent, a topoisomerase inhibitor, a platinum drug, a molecular targeted drug, which have cytotoxic activities are particularly preferred. Specific examples of particularly preferred anti-cancer agents include gemcitabine, 5-FU, CPT-11, etoposide, cisplatin, oxaliplatin, paclitaxel, docetaxel, dacarbazine, doxorubicin, bevacizumab, cetuximab, anti-endothelial growth factor receptor 2 inhibiting antibody, and epidermal growth factor tyrosine kinase inhibitor.

The anti-MFG-E8 antibody and the anti-cancer agent (other than the anti-MFG-E8 antibody) may be used in a single formulation or separate formulations. In the case of separate formulations, the administration routes thereof may be different from each other (e.g., injection and oral drug). The anti-MFG-E8 antibody and the anti-cancer agent may be administered concomitantly, or one of them administered before administration of the other. That is, the anti-MFG-E8 antibody may be administered before or concomitant with or after administration of the anti-cancer agent. In the case where two agents are not administered concomitantly, in one preferred manner, the anti-cancer agent is administered for a certain period, and during administration or after administration of the agent, the anti-MFG-E8 antibody is administered. Specifically, the anti-MFG-E8 antibody is administered within two weeks after start of administration of the anti-cancer agent, preferably within one week, more preferably within three days.

The immunogenicity of apoptosis tumor cells induced by chemotherapy employing, for example, the anti-cancer agent is effectively attained through MFG-E8 inhibition due to the anti-MFG-E8 antibody, whereby anti-tumor immunity which the body intrinsically possesses can be suitably realized. In addition, the relapse of the tumor after the treatment could be suppressed with this therapy. In consideration of the action and effect of the anti-MFG-E8 antibody, when the chemotherapy employing the anti-cancer agent or similar therapy is performed concomitant with or prior to administration of the anti-MFG-E8 antibody, the combinatory therapy becomes very effective.

As used herein, the concept "combination of the anti-MFG-E8 antibody and the anti-cancer agent (other than the anti-MFG-E8 antibody)" is not limited to the case where the two ingredients assume a single formulation. The concept "combination of the anti-MFG-E8 antibody and the anti-cancer agent" also encompasses includes the case where the anti-MFG-E8 antibody is administered as a single formulation, so long as the antibody is used in combination with the anti-cancer agent at the aforementioned timing for the purpose of potentiation of the anti-cancer agent. Note that, as mentioned in detail hereinbelow, the anti-cancer agent (other than the anti-MFG-E8 antibody) may consist of a combination of two or more agents.

Moreover, the concept "combination of the anti-MFG-E8 antibody and the anti-cancer agent" also refers to the case in which the anti-MFG-E8 antibody is used at a specific timing with administration of the anti-cancer agent, and the anti-MFG-E8 antibody serves as a combinatory agent for potentiating the anti-cancer agent (or an anti-tumor effect-potentiator). Also, the concept "combination of the anti-MFG-E8 antibody and the anti-cancer agent" means the case in which the anti-MFG-E8 antibody serves as a predominant ingredient of a cancer therapeutic drug, and the anti-cancer agent serves as a combinatory agent which can effectively attain the anti-tumor immune responses of the anti-MFG-E8 antibody (or an initiator), and the anti-cancer agent (combinatory agent) and the anti-MFG-E8 antibody (main cancer therapeutic agent) are administered at specific timings.

Examples of the cancer therapy other than administration of the anti-cancer drug include surgical operation, radiotherapy (including gamma knife treatment, cyber knife treatment, boron neutron capture therapy, and proton radiation therapy/heavy ion therapy), MR-guided focused ultrasound surgery, cryotherapy, radio frequency ablation, ethanol-injection, and artery embolization.

The aforementioned cancer therapy and administration of the anti-MFG-E8 antibody may be performed concomitantly, or one of them may be performed before performance of the other. In a preferred mode, a predetermined radiotherapy is performed, and then the anti-MFG-E8 antibody is administered. So long as the administration of the anti-MFG-E8 antibody and the cancer therapy (that does not employ the antibody) are performed at the aforementioned timing, the concept "combination of the anti-MFG-E8 antibody and the cancer therapy (that does not employ the anti-MFG-E8 antibody)" also encompasses this mode. Notably, the "cancer therapy (that does not employ the antibody)" may be a combinatorial therapy of a plurality of methods, and the "cancer therapy (that does not employ the antibody)" may be combined with the aforementioned administration of "the anti-cancer agent (other than the anti-MFG-E8 antibody)."

The anti-MFG-E8 antibody may be used in combination with, for example, a cellular therapy employed in cancer therapy. In the case of combination with a cellular therapy, the anti-MFG-E8 antibody may be added to cells employed in the cellular therapy during its preparation step. Alternatively, the anti-MFG-E8 antibody may be administered to a patient when the prepared cells are returned to the patient.

The anti-cancer drug of the present invention is effective for a variety of cancers of mammals including human, such as epithelial cancers; e.g., pharyngeal cancer, laryngeal cancer, tongue cancer, lung cancer, breast cancer, esophageal cancer, stomach cancer, colon cancer, uterus cancer, ovarian cancer, liver cancer, pancreatic cancer, gallbladder cancer, kidney cancer, prostate cancer, malignant melanoma, and thyroid gland cancer, and non-epithelial cancers; e.g., osteosarcoma, chondrosarcoma, rhabdomyoma, leiomyoma, liposarcoma, angiosarcoma, fibrosarcoma, leukemia, malignant lymphoma, and myeloma.

As mentioned above, the anti-MFG-E8 antibody effectively induces anti-tumor immune responses and inhibits the relapse of the tumor, through potentiating immunogenicity of chemotherapy-induced apoptosis tumor cells by inhibition of MFG-E8. Therefore, when apoptosis of tumor cells are induced by chemotherapy, radiotherapy, etc., a considerable anti-tumor effect of the anti-MFG-E8 antibody can be expected. When the anti-MFG-E8 antibody is combined with a cancer therapy to which a multi-drug therapy, a radio-chemotherapy, etc. have been established as a standard therapy, potentiation of tumor-shrinking effect and enhancement of disease-free relapse-free rate can be realized.

Examples of the candidate combination include FOLFOX (5-FU+oxaliplatin) in colorectal cancer; fluorouracil drug (containing tegafur-gimeracil-oteracil potassium)+cisplatin in stomach cancer; chemo-/radio-combinatorial therapy in esophageal cancer, head and neck cancer, and uterus cancer (esophageal cancer: fluorouracil+cisplatin, head and neck cancer: fluorouracil+cisplatin+taxan, uterus cancer: carboplatin, etc.); a combination of gemcitabine and radiotherapy in bile or pancreatic duct cancer; CDDP+taxan/vinorelbine/gemcitabine or the like in non-small cell lung carcinoma; CDDP+etoposide in small cell lung carcinoma; anthracycline antibiotic+cytarabine in acute myelocytic leukemia; R-CHOP therapy (rituximab, cyclophosphamide, anthracycline antibiotic, vincristine, predonine) in malignant lymphoma; multi-drug chemotherapy (CAF therapy: cyclophosphamide, anthracycline antibiotic, fluorouracil, etc.) and taxan+herceptin in breast cancer; and Tamozolomide+whole brain irradiation in medulloblastoma.

The anti-cancer drug of the present invention may be formed to a drug formulation, with a pharmacologically acceptable carrier well known in the art, through mixing, dissolution, granulation, tabletizing, emulsification, encapsulation, lyophilization, etc.

For oral administration, the anti-MFG-E8 antibody may be formed to a drug formulation with a pharmacologically acceptable solvent, excipient, binder, stabilizing agent, dispersant, etc., in the dosage form of tablet, pill, sugar-coated tablet, soft capsule, hard capsule, solution, suspension, emulsion, gel, syrup, slurry, etc.

For parenteral administration, the anti-MFG-E8 antibody may be formed to a drug formulation with a pharmacologically acceptable solvent, excipient, binder, stabilizing agent, dispersant, etc., in the dosage form of injection solution, suspension, emulsion, cream, ointment, inhalation, suppository, etc. In injection preparation, the therapeutic drug of the present invention may be dissolved in an aqueous solution, preferably in a physiologically adaptable buffer such as Hanks' solution, Ringer's solution, or physiological saline. A composition of the drug of the invention may be in the form of suspension, solution, emulsion, etc. in an oily or aqueous vehicle. Alternatively, the anti-MFG-E8 antibody may be prepared as powder, and the antibody may be reconstituted with sterilized water or the like to provide aqueous solution or suspension upon use. For administration via inhalation, the anti-MFG-E8 antibody may be prepared as powder, and the powder may be mixed with an appropriate base such as lactose or starch, to thereby form a powder mixture. Suppository preparations may be produced through mixing the anti-MFG-E8 antibody with a suppository base such as cacao butter. Further, the therapeutic drug of the present invention may be prepared as a sustained-release formulation through enclosure in a polymer matrix.

The daily dose of the anti-MFG-E8 antibody, which varies in accordance with the symptom, administration route, body weight, age, etc. of a patient, is preferably, for example, 1 μg to 500 mg for an adult. The dose of the anti-cancer agent (other than the antibody) is preferably an effective amount thereof or 0.01 to 1 times the amount. The dose of the cancer therapy (not employing the antibody), for example the radiation dose of radiotherapy, may be reduced 0.1 to 0.8 times.

No particular limitation is imposed on the administration route of the anti-cancer drug of the present invention, and parenteral administration is generally employed. For example, injection (hypodermic, intravenous, intramuscle, intraperitoneal, etc.), percutanous administration, transmucosal administration, transnasal administration, or pulmonary administration is employed. However, needless to say, the anti-cancer drug of the present invention may also be administered orally.

The action mechanism of the antitumor effects of the anti-MFG-E8 antibody of the present invention has not yet been elucidated completely. However, one conceivable central mechanism is that the antibody activates intra-tumor and systemic anti-tumor immune responses, whereby anti-tumor immune reactions involving induction of tumor-specific cytotoxic T cells is induced and promoted.

Thus, the anti-MFG-E8 antibody activates immune responses to target cells, to thereby induce cytotoxic T cells, whereby immune reaction with respect to the target cells is induced and promoted. Thus, through combination of the anti-MFG-E8 antibody with a drug or a therapy that is toxic to the target cells, immune reaction with respect to the target cells is effectively induced. Therefore, the drug of the present invention can be employed as a drug for induction of specific immune responses to a variety of target cells to be removed such as cancer cells. The induction of specific immune responses by the anti-MFG-E8 antibody is realized by suppressing a tolerance pathway by the mediation of $\alpha_v\beta_3$ integrin present on the surface of antigen-presenting cells and switching the pathway to an immune potentiating pathway by the mediation of an Fc-receptor. As used herein, the term "antigen-presenting cells" encompasses dendritic cells, a monocytes, and macrophages.

EXAMPLES

The present invention will next be described in more detail by way of examples, which should not be construed as limiting the invention thereto.

Example 1

Synergistic Tumor-shrinking Effects by Anti-cancer Agent and Anti-MFG-E8 Antibody (Method)

The MC 38, mouse colon carcinoma cells or B16, melanoma cells were subcutaneously injected to the back of 6-week-old C57Bl/6 mice ($1\times10^5$ cells/mouse). After the tumor diameter (longer diameter) reached 5 mm (25 to 30 mm$^2$) (day 10), an anti-cancer agent and/or an anti-MFG-E8 antibody were/was intraperitoneally administered to each mouse on day 10, day 13, and day 16 according to any of the following protocols. The experiments according to each protocol were performed twice. The employed anti-MFG-E8 antibody was a blocking antibody commercially available from MBL. In protocols 1 to 4, MC38 was used, and B16 melanoma was used in protocol 5.

Protocol 1:
  Gemcitabine (GEM): 4 mg/kg
  Gemcitabine (GEM): 1 mg/kg
  Anti-MFG-E8 antibody: 1 mg/kg
  Gemcitabine (GEM): 4 mg/kg+anti-MFG-E8 antibody: 1 mg/kg
  Gemcitabine (GEM): 1 mg/kg+anti-MFG-E8 antibody: 1 mg/kg Protocol 2:
  CPT-11: 1 mg/kg
  5-FU: 0.1 M
  Anti-MFG-E8 antibody: 1 mg/kg
  CPT-11: 1 mg/kg+anti-MFG-E8 antibody: 1 mg/kg
  5-FU: 0.1 M+anti-MFG-E8 antibody: 1 mg/kg Protocol 3:
  Epidermal growth factor receptor tyrosine kinase 1 (EGFR-TK1): 40 mg/g
  Anti-vascular endothelial growth factor receptor-2 monoclonal antibody (α-VEGFR-2Ab): 40 mg/kg
  Anti-MFG-E8 antibody: 1 mg/kg Protocol 4:
  Irradiation (XRT): 3 Gy/day×5
  Anti-MFG-E8 antibody: 1 mg/kg
Protocol 5:
  Doxorubicin (Dox): 5 mg/kg
  Etoposide (Etop): 2 mg/kg
  Anti-MFG-E8 antibody: 1 mg/kg
(Results)

When an anti-cancer agent alone was administered, tumor growth was significantly suppressed for 5 to 10 days after administration, as compared with a non-treated group. However, a similar tumor growth profile as shown in the non-treated group was observed thereafter. This tendency was also observed in the cases of administration of GEM, 5FU, CPT-11, doxorubicin, etoposide, EGF-TK1, and α-VEGFR-2Ab (anti-cancer agents) and also in the case of radiotherapy. Thus, anti-tumor effects provided by any of the anti-cancer agents are transient, and a long-lasting anti-tumor effects cannot be attained by such anti-cancer agent alone (FIGS. 1 to 5).

When an anti-MFG-E8 antibody alone was administered, significant but mediocre anti-tumor effects were observed, as compared with a non-treated group. However, this suppression effect was weaker as compared with the case of administration of an anti-cancer agent or the case of radiotherapy (FIGS. 1 to 5).

Anti-cancer agent/anti-MFG-E8 antibody combinatory administration groups and radiotherapy/anti-MFG-E8 antibody combined groups exhibited significantly potent tumor growth-suppression effect. Differing from the anti-cancer agent alone administration groups or the radiotherapy alone groups, this potent effect was maintained for a long period after termination of the relevant therapy. For example, in the gemcitabine (4 mg/kg)/anti-MFG-E8 antibody combined group and the 5-FU/anti-MFG-E8 antibody combined group, no substantial tumor growth was observed to the point in time 35 days after administration. The similar results were obtained for all types of the employed anti-cancer agents (anti-EGFR antibody, anti-VEGFR antibody, etc.) (FIGS. 1 to 5).

Thus, these experiments have revealed that inhibition of MFG-E8 activity provided by the anti-MFG-E8 antibody dramatically improves the anti-tumor effects of the tested anti-cancer agents or employed radiotherapy. It has never been expected that an excellent anti-tumor effect can be attained through combination of an anti-cancer agent or radiotherapy with an anti-MFG-E8 antibody without administering tumor antigens.

Example 2

Studies on Tumor Infiltrating Lymphocytes for Surface Phenotypes Related to Immune Functions (Method)

The tumor models to which the same MC38 colon carcinoma cells had been subcutaneously administered were subjected to therapy protocols. One week after completion of protocol (day 23), the tumor tissue was collected from each mouse. The thus-obtained tissue was treated with collagenase I, and the lymphocytes present in the tumor tissue were separated and recovered through the density gradient method employing Lymphoprep. The surface antigens related to the activities of lymphocytes in tumor tissue were examined using flow cytometry in terms of the following items.

Memory activity of CD4-positive helper T cells and CD8-positive cytotoxic T cells (expression of CD44)
  Proportion of CD11b•Gr-1 positive cells (immature myeloid cells), which are key cells to suppression of T cell activity
  Proportion of CD11c-positive cell fraction serving as a marker for dendritic cells which contribute to potentiation of anti-tumor T cell activity
  Evaluation of dendritic cell activity: proportions of CD11b and CD86 positive fractions
(Results)

Taking the 5-FU groups as typical examples, the results will be described. Similar results were obtained for the other treatment groups.

Figure 6:
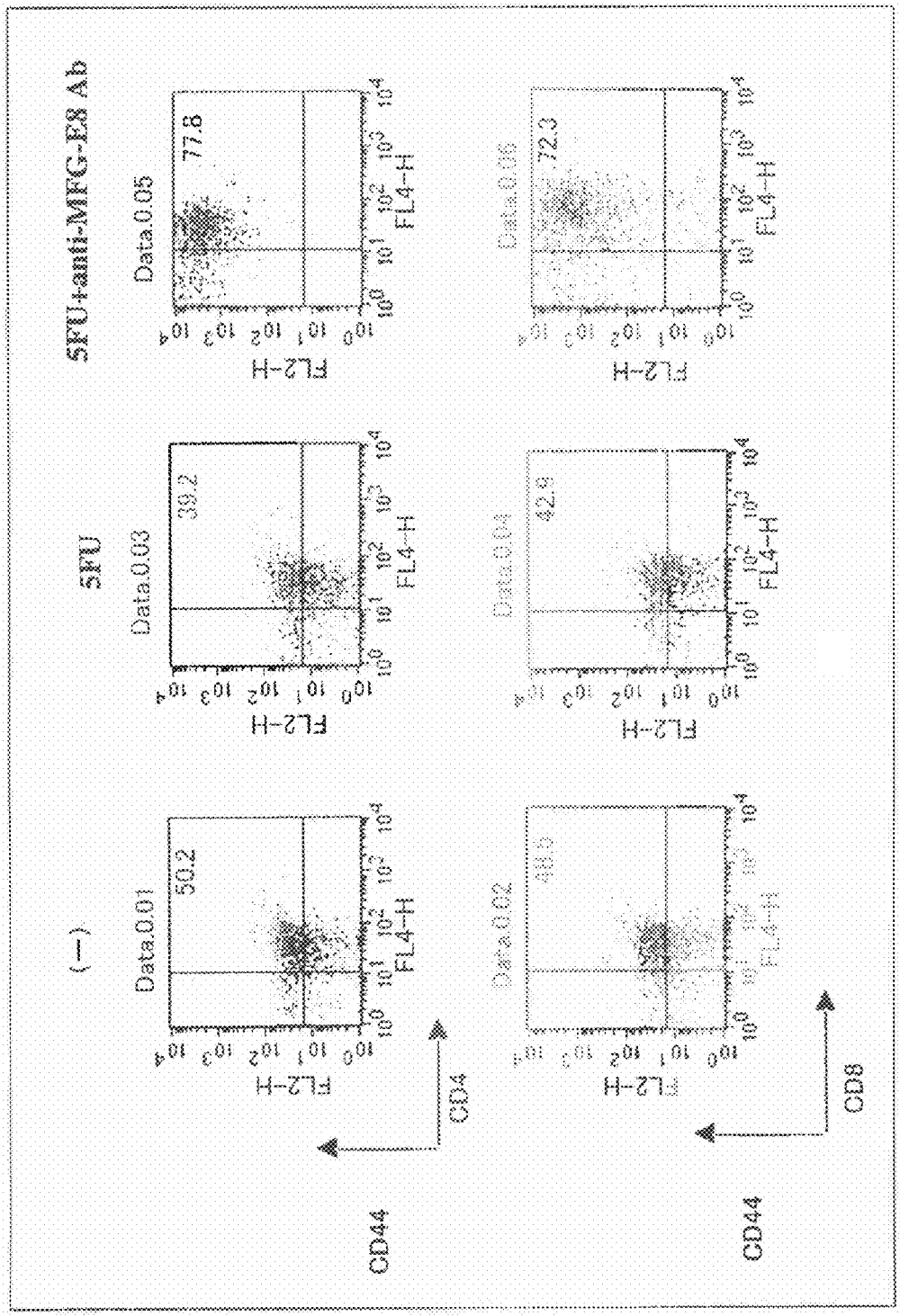
[FIG. 6] Graphs showing the results of flow cytometry of surface antigens relating to activities of intratumor lymphocytes (CD4 and CD8) when 5-FU and anti-MFG-E8 antibody were administered to the same tumor models as shown in FIG. 1.
Figure 7:
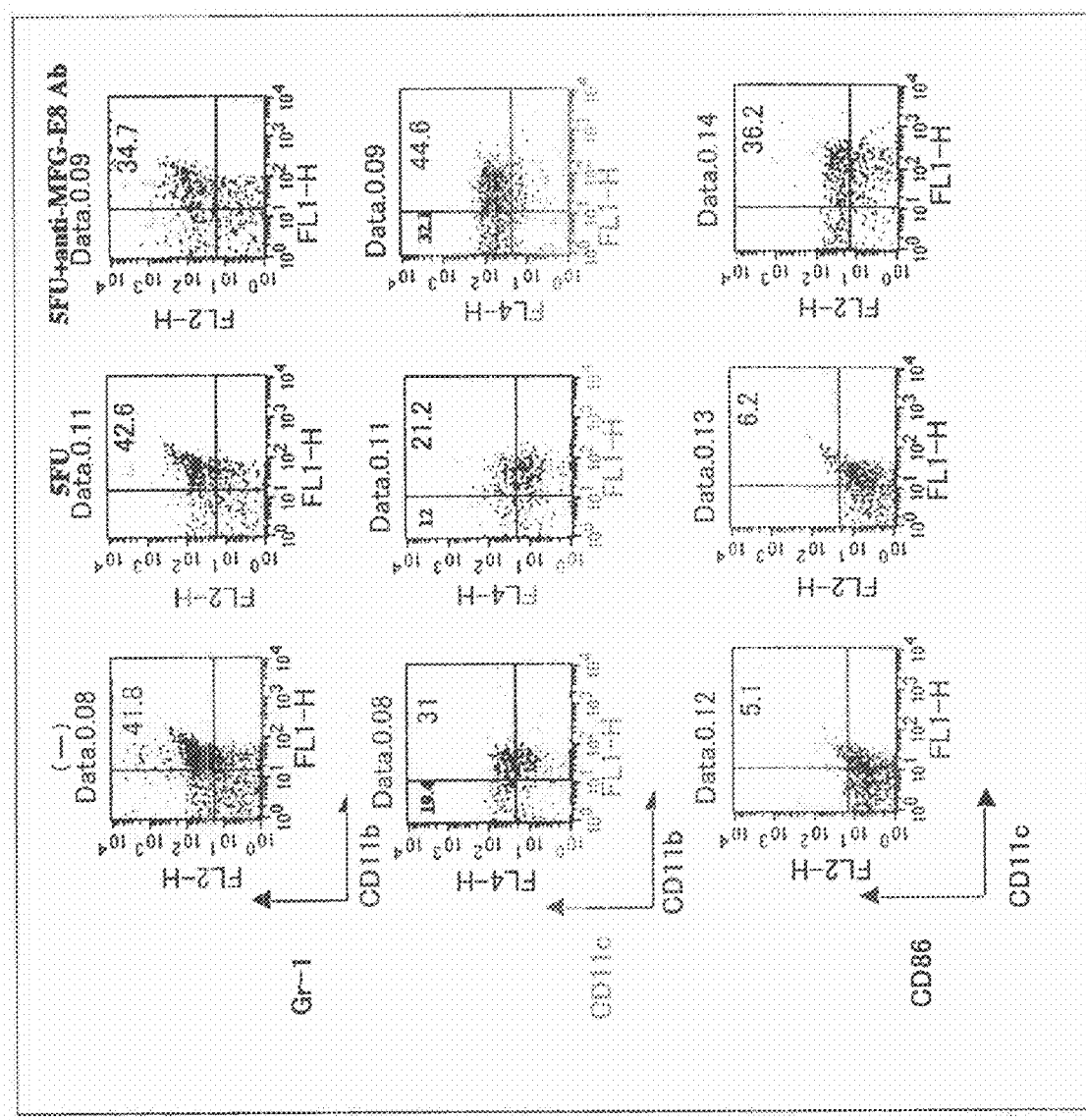
[FIG. 7] Graphs showing the results of flow cytometry of surface antigens relating to activities of intratumor lymphocytes (CD11b and CD11c) when 5-FU and anti-MFG-E8 antibody were administered to the same tumor models as shown in FIG. 1.

As compared with the non-treated group, the groups treated with anti-cancer agent alone exhibited no significant change in proportions of T cells, immature myeloid cells, or dendritic cells (FIGS. 6 and 7). This tendency was the same as in the case of the group treated with anti-MFG-E8 antibody alone.

In the cases of the group of an anti-cancer agent/anti-MFG-E8 antibody combinatory administration, the following charges were observed.

T cell memory activity (expression of CD44) was increased (FIG. 6). This shows induction of active competence of T cells invading the tumor.

The number of dendritic cells increased considerably, and the activity thereof was considerably potentiated (FIGS. 6 and 7). Conceivably, invasion of the dendritic cells upon the tumor and dendritic cell activity were induced. Such circumstances are suitable for potentiating specific T cell immune response.

Thus, through combinatory use of an anti-cancer agent and the anti-MFG-E8 antibody, the anti-tumor immune responses (i.e., immune response specific to the target tumor) in the tumor were thought to be potentiated. It was suggested that a local environment of the tumor might be involved in such considerable potentiation of tumor growth-suppression effect observed in the combinatory use groups.

Example 3

Evaluation of the Effects of the Antibody in Terms of Enhancement of Immunological Activity of Lymphocytes in the Spleen In addition to changes in local (tumor site) immune responses, changes in systemic immune responses were also investigated through the following procedure. Spleen cells (i.e., typical peripheral lymphatic tissue) were analyzed. Specifically, the spleen was removed from each of the mice which had been analyzed in terms of immunological activity of tumor infiltrating lymphocytes, and spleen cells were isolated from the removed spleen. The activities of CD4-positive helper T cells and CD8-positive cytotoxic T cells were investigated through flow cytometry in terms of the following items.

Memory activity (expression of CD44)
  Cytokine production profile: Interferon-γ (IFN-γ; marker for immune activation)
  :Interleukin-10 (IL-10; marker for immune suppression)
(Results)

Figure 8:
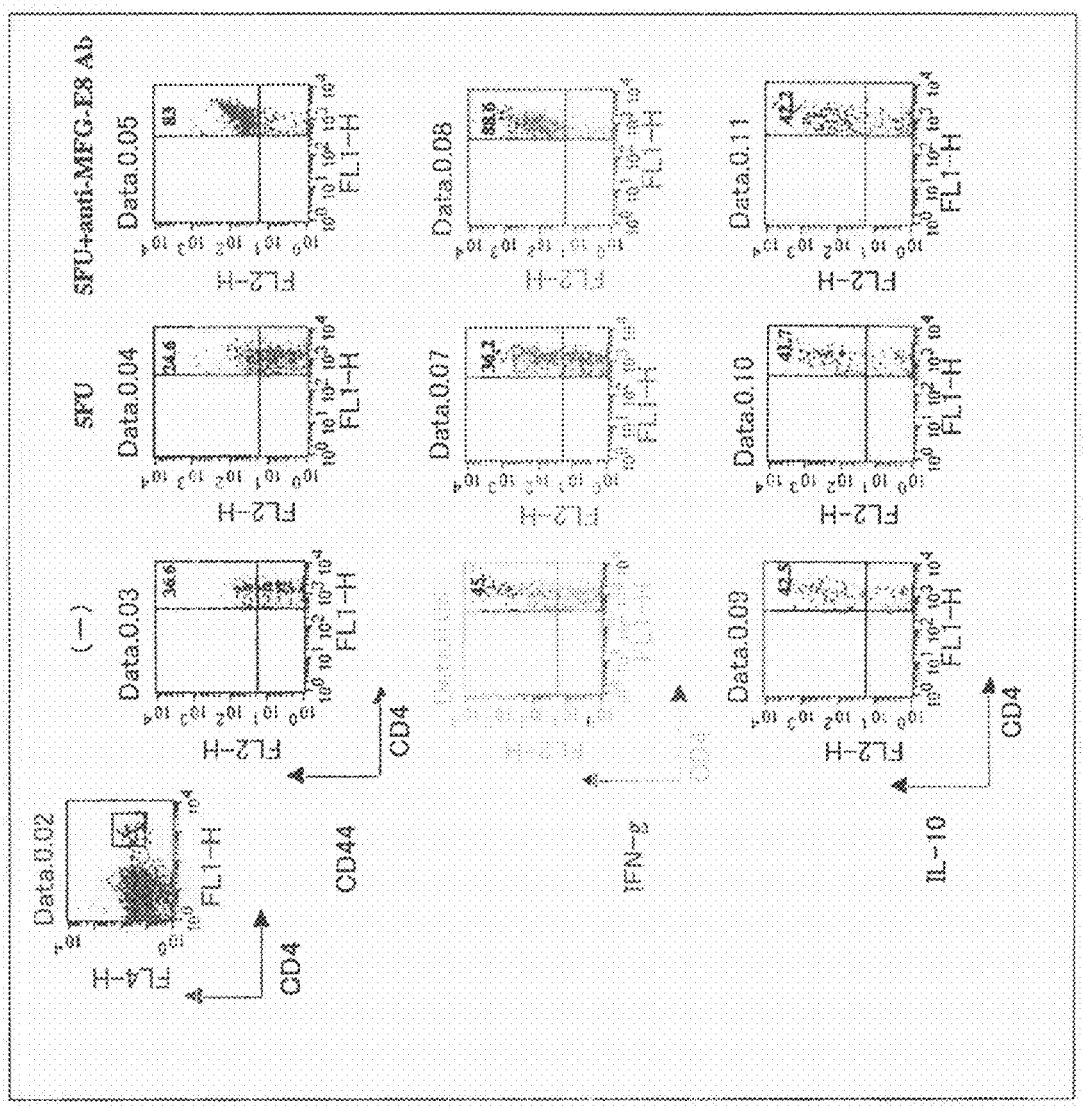
[FIG. 8] Graphs showing the results of flow cytometry of surface antigens relating to activities of splenic lymphocytes (CD4) when 5-FU and anti-MFG-E8 antibody were administered to the same tumor models as shown in FIG. 1.
Figure 9:
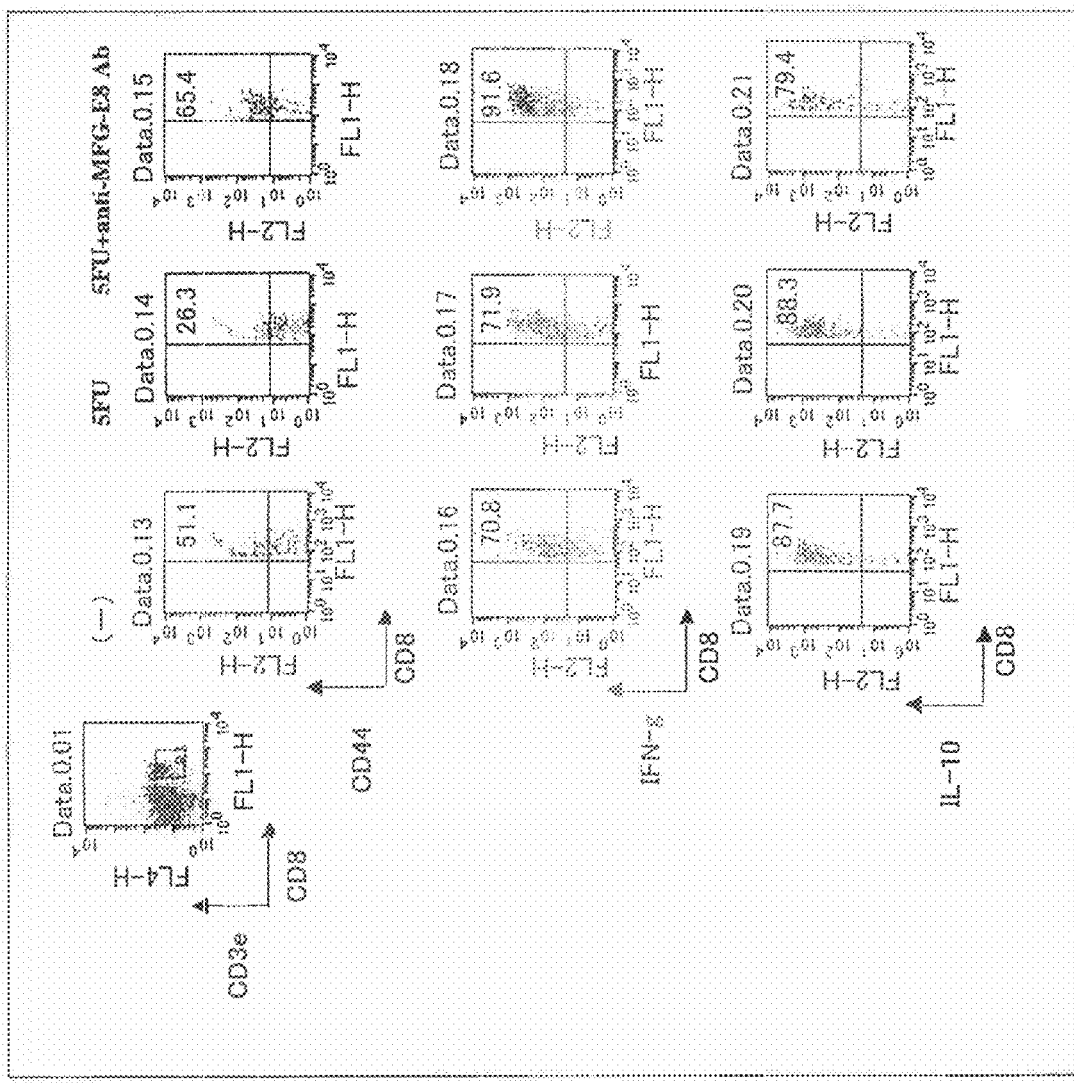
[FIG. 9] Graphs showing the results of flow cytometry of surface antigens relating to activities of splenic lymphocytes (CD8) when 5-FU and anti-MFG-E8 antibody were administered to the same tumor models as shown in FIG. 1.

As compared with the non-treated group, the group treated with the anti-cancer agent alone exhibited no considerable change in proportions of T cells, immature myeloid cells, and dendritic cells (FIGS. 8 and 9).

The tendency was the same as that observed in the group treated with anti-MFG-E8 antibody alone.

In the group treated with the combination of the anti-cancer agent and the anti-MFG-E8 antibody, the spleen cells clearly exhibited enhanced expression of CD44 and production of IFN-γ. Regarding IL-10 reaction, there was no significant difference between the non-treated group and the group treated with anti-cancer agent alone (FIGS. 8 and 9).

Thus, through employment of the anti-cancer agent and the anti-MFG-E8 antibody in combination, anti-tumor immune response was found to be activated not only locally (tumor site) but also systemically.

Example 4

Studies on Induction of Tumor-specific Cytotoxic T Cells Through Combinatory Use of Anti-MFG-E8 Antibody and Anti-cancer Agent (Method)

Lymph nodal cells were isolated from each of the tumor-bearing mice of the non-treated group, the anti-MFG-E8 antibody administration group, the anti-cancer agent administration group, and the anti-cancer agent/antibody combinatory administration group. The thus-isolated cells were co-cultured with irradiated (200 Gy) MC38 colon carcinoma cells at a ratio of 10:1. Five days after the start of culture, the lymph node cells and $^{51}$Cr-labeled target tumor cells were mixed-cultured for four hours. Subsequently, the amount of $^{51}$Cr released to the culture supernatant was measured by means of a γ-scintillator, to thereby determine cytotoxic activities against the tumor cells.

(Results)

Figure 10:
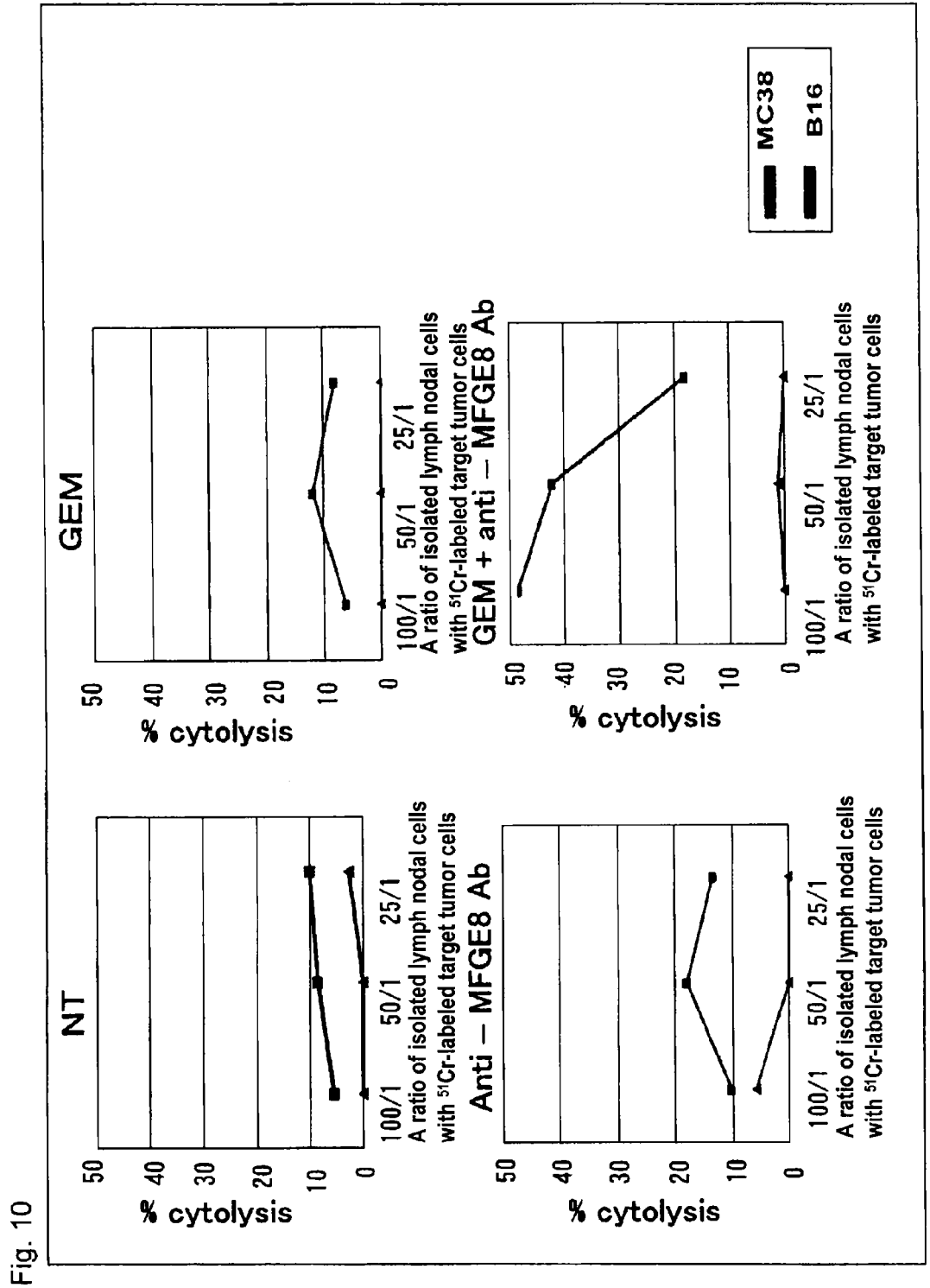
[FIG. 10] Graphs showing tumor-specific cytotoxic activities of lymphocytes in the lymphonodes, when anti-cancer agent (other than anti-MFG-E8 antibody) and anti-MFG-E8 antibody were administered to the same tumor models as shown in FIG. 1. B16 represents B16 cells, and MC38 represents MC38 cells.

The lymph node cells derived from the anti-MFG-E8 antibody treatment group were found to exhibit cytotoxic activity to MC38. The lymph node cells derived from the anti-cancer agent/anti-MFG-E8 antibody combinatory treatment group were found to have an MC38-specific cytotoxicity at the significantly higher extent. In contrast, no substantial cytotoxic activity on B16 malignant melanoma cells was induced (FIG. 10).

Thus, combinatory use of the anti-cancer agent and the anti-MFG-E8 antibody was found to promote the induction of tumor-specific cytotoxic lymphocytes.

Example 5

In vitro Studies on Potentiation of Antigen-specific T Cell Activity Through Modification of Dendritic Cell Activity by MFG-E8

(Method)

The mechanisms of activation of dendritic cells and T cells through employment of the anti-MFG-E8 antibody and the anti-cancer agent, such activation having been observed in vivo, were further investigated in vitro by using a mixed culture system.

Specifically, ovalbumin (OVA) was employed as a model antigen. In a specific procedure, bone marrow cells were collected from DO11.10 (MHC class II-restricting OVA antigen transgenic mice), and differentiation to dendritic cells was induced with granulocyte-monocyte colony-stimulating factor (GM-CSF). Seven days after the initiation of the differentiation induction, the cells were treated with MFG-E8 recombinant protein (100 µg/mL) or anti-MFG-E8 antibody (20 µg/mL). Thereafter, on day 8, the thus-treated cells were pulsed with MHC class II OVA-restricting OVA peptide (5 mg/mL) or a negative control peptide (HSA) for six hours. The resultant cells were admixed with naive CD4+ positive T cells derived from syngeneic (Balb/c) mice in such an amount that the ratio of dendritic cells to CD4+ T cells was adjusted to 1:10, and the cell mixture was cultured in the presence of an anti-CD3 antibody (0.1 µg/mL). Seventy-two hours after, the activity of T cells was determined through flow cytometry, in terms of intracellular expression of IFN-γ and IL-10.

(Results)

Non-treated Dendritic Cells:

T cell activity was found to be enhanced by OVA-specific dendritic cells (Since both IFN-γ and IL-10 increased, both immunological activity and immune suppression performance were thought to be activated).

MFG-E8-Stimulated Dendritic Cells:

As compared to the control group, suppression of OVA-specific IFN-γ production and potentiation of IL-10 production were observed (suppression of antigen-specific immune response was confirmed).

When the activities of MFG-E8 secreted from dendritic cells were blocked with anti-MFG-E8 antibody, potentiation of OVA-specific IFN-α production and suppression of IL-10 production were observed (activation of antigen-specific immune response was confirmed).

Figure 11:
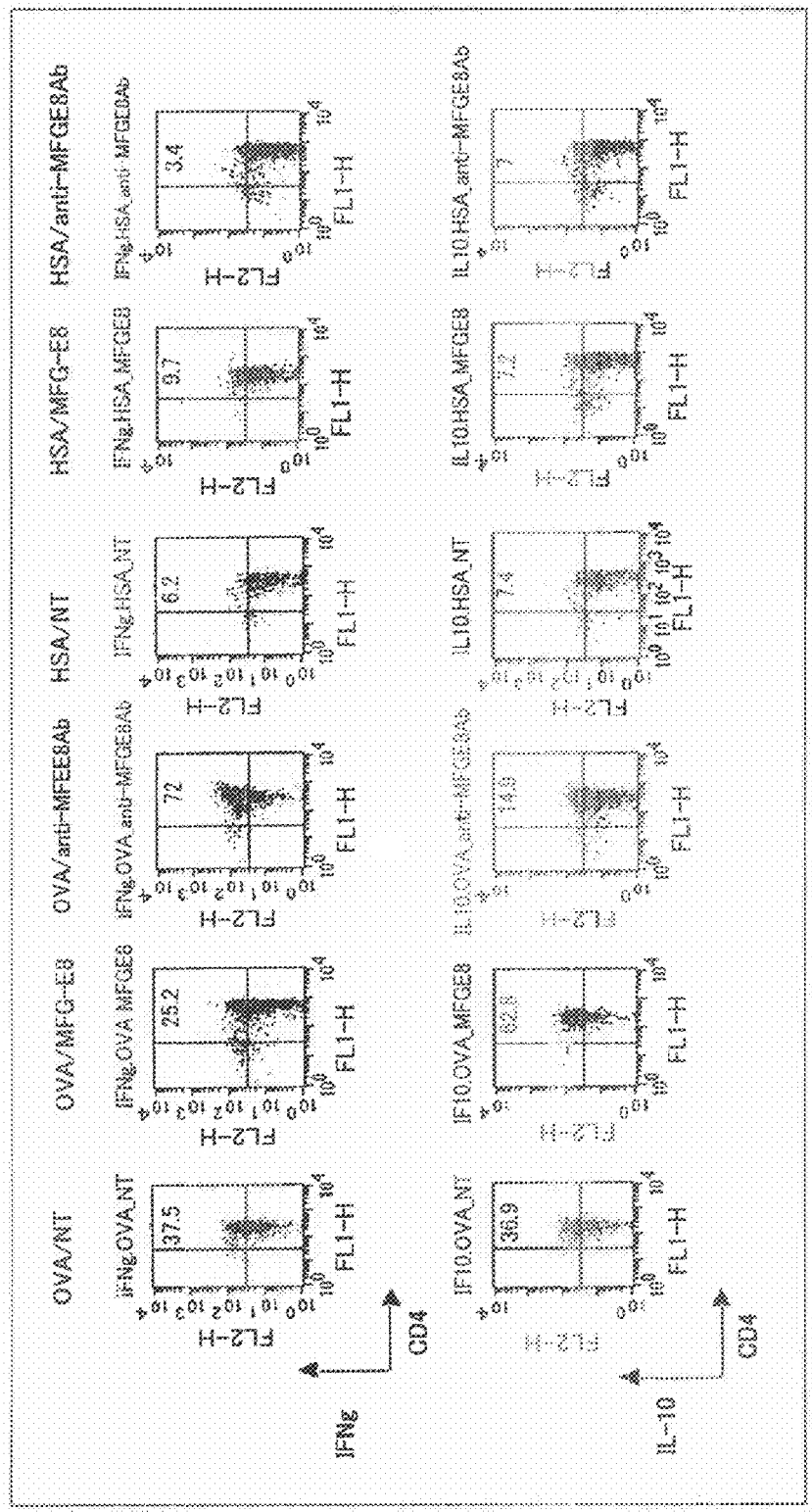
[FIG. 11] Graphs showing activation of T cell observed through flow cytometry of cells of OVA transgenic mice, the state being represented by intracellular expression of IFN-γ (IFNg) and IL-10.

Thus, it has been elucidated that MFG-E8 directly acts on dendritic cells, to thereby make the immunological activity thereof negative, and that neutralization by the anti-MFG-E8 antibody activates the immune response of dendritic cells in an antigen-specific manner. The function of the anti-MFG-E8 antibody was also observed in peptide-pulsed dendritic cells. Therefore, the activation mechanism is thought to involve regulation of co-stimulation molecules, which is a function of dendritic cells other than antigen-presenting function (FIG. 11 (IFNg: IFN-γ)).

Example 6

Studies on Induction of MFG-E8 Expression (Secretion) from Tumor Cells with Anti-cancer Agent (Method)

In order to examine the effects of anti-cancer drugs on the susceptibility to MFG-E8 inhibition, each of the anti-cancer agents (Doxorubicine, GEM, 5-FU, CPT-11, etc.) was administered to MC38 colon carcinoma cells and normal fibroblast cells (NIH3T3 and primary fibroblast). Twenty-four hours after, expression of MFG-E8 was investigated through intracellular flow cytometry and ELISA of the cell culture supernatant.

(Results)

Figure 12:
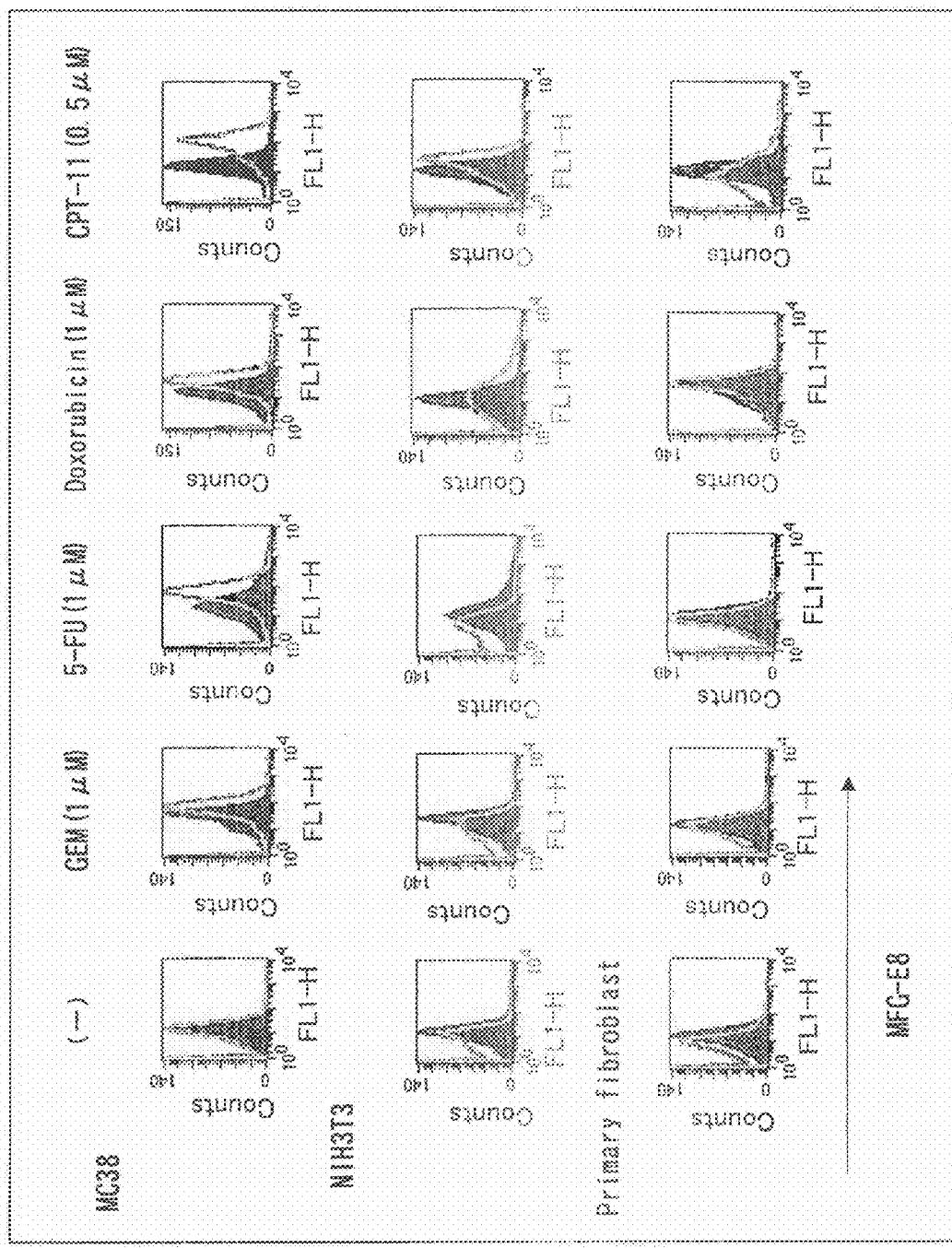
[FIG. 12] Graphs showing expression of MFG-E8 in tumor cells and non-tumor cells treated with an anti-cancer agent (other than the antibody).
Figure 13:
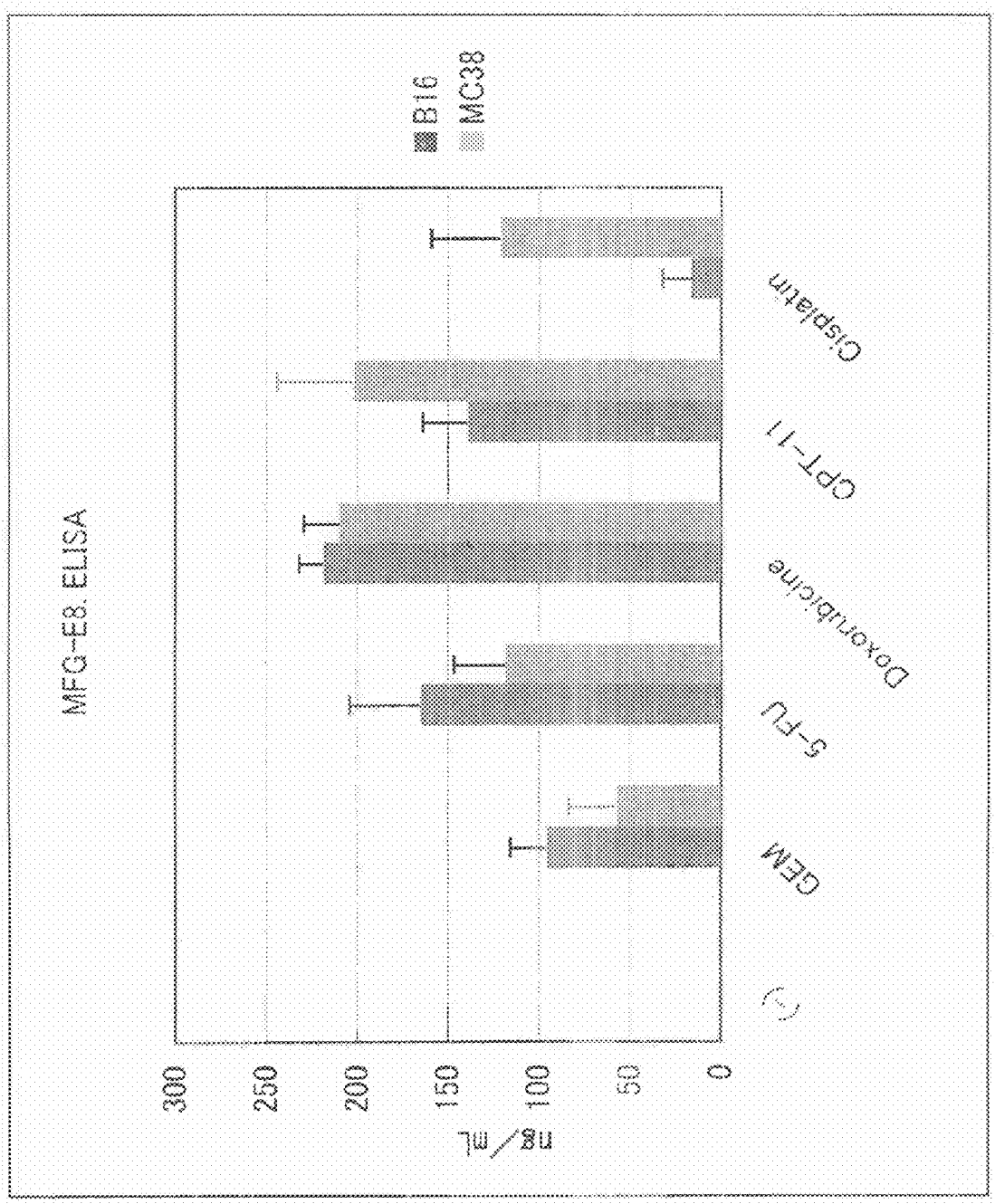
[FIG. 13] A graph showing expression of MFG-E8 in tumor cells treated with an anti-cancer agent (other than the antibody).

With the administration of any of the anti-cancer agents, MFG-E8 production of MC38 increased significantly. In contrast, enhancement of MFG-E8 expression with the anti-cancer agents was not observed in NIH3T3 and Primary fibroblast, which are non-carcinoma cells (FIG. 12). In B16 melanoma cells, induction of MFG-E8 production with the anti-cancer agents was observed (FIG. 13).

Thus, MFG-E8 production of tumor cells was found to be induced by the anti-cancer agents. In consideration of the hitherto elucidated functions of MFG-E8, induction of MFG-E8 production is suggested to be one conceivable mechanism of acquiring resistance with respect to therapy employing such an anti-cancer agent.

Example 7

Studies on Effect of Anti-MFG-E8 Antibody on Induction of Tumor Cell Apoptosis by Anti-cancer Agent (Method)

Each of the anti-cancer agents (GEM: 1M, CPT-11: 0.5M, and 5FU: 1M) was added to the culture of MC38 colon carcinoma cells. In addition to the anti-cancer agent, an anti- MFG-E8 blocking antibody (20 μg/mL) or an IgG antibody serving as a negative control was also added. The cells were cultured for 48 hours in the absence of serum. After culturing, cell death rate was quantitatively determined with flow cytometry.
(Results)

In the anti-cancer agent-free group, significant induction of tumor cell apoptosis was observed with the anti-MFG-E8 antibody. However, the magnitude of the effect was lower, as compared with the same effect provided by the anti-cancer agent.

Among the anti-cancer agent administration groups, significant enhancement of tumor cell apoptosis was observed in the anti-cancer agent/antibody combinatory administration group, as compared with extent of the apoptosis observed in the control group. Similar extent of enhancement was obtained when any of the anti-cancer agents was used in combination with anti-MFG-E8 antibody.

Figure 14:
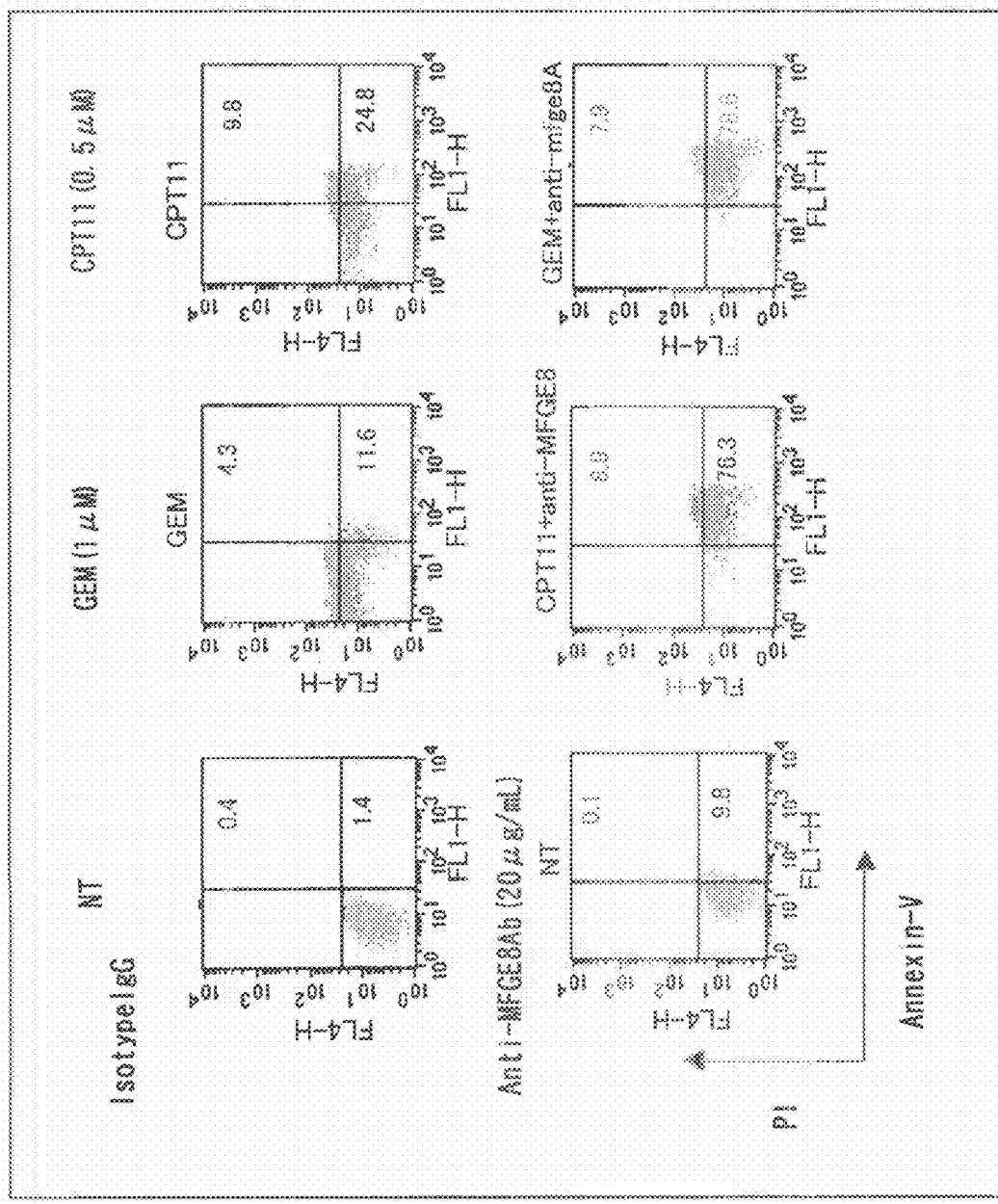
[FIG. 14] Graphs showing the effects of anti-MFG-E8 antibody on induction of apoptosis of tumor cells (mouse colon carcinoma cells (MC38)) caused by an anti-cancer agent other than anti-MFG-E8 antibody.

Thus, the anti-tumor effect with MFG-E8 inhibition has been suggested to involve indirect tumor shrinkage by potentiation of immunity and direct induction of tumor cell apoptosis by the anti-cancer agent (FIG. 14).

Example 8

In vivo Apoptosis Induction (Method)

In vivo apoptosis was measured through the following procedure. In the presence or absence of an anti-MFG-E8 antibody, MC38 or B16 tumor (25 mm$^2$) was treated with gemcitabine or dacarbazine (10 mg/kg). Four days after the treatment, the tumor was removed and homogenized. The caspase 3 activity of the tumor homogenate was determined by means of a colorimetric assay kit (Invitrogen).
(Results)

Figure 15:
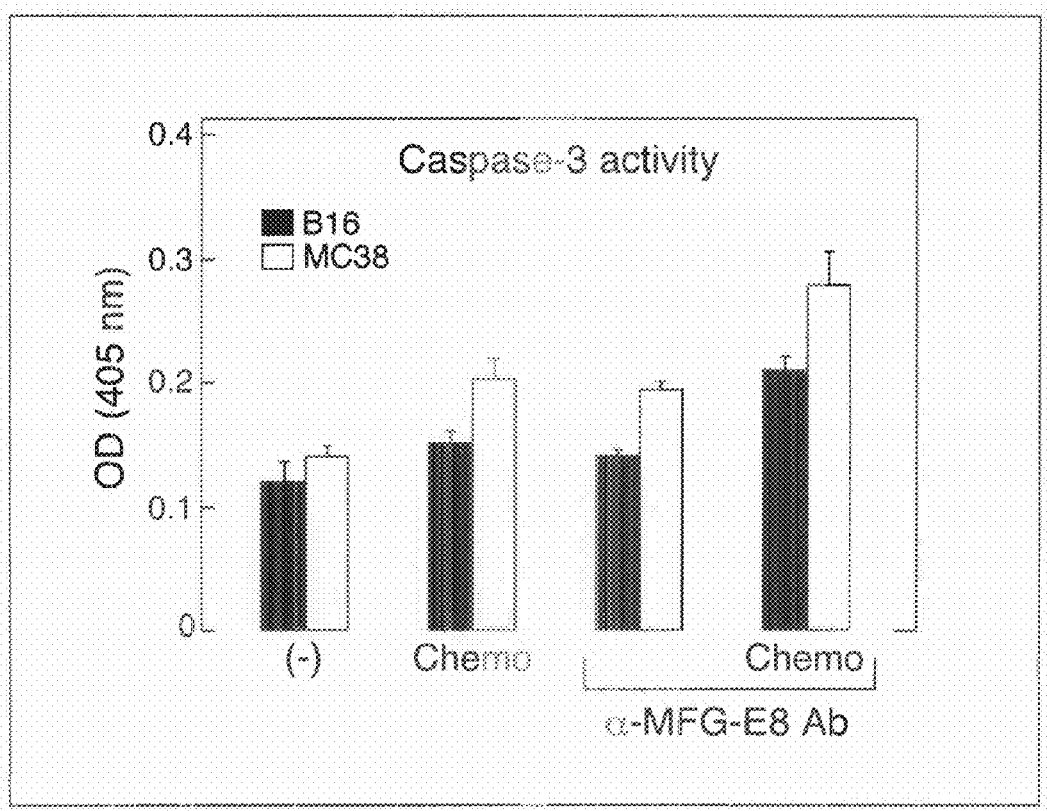
[FIG. 15] A graph showing the action of activating caspase 3 as an apoptosis marker upon combined administration of anti-MFG-E8 antibody and an anti-cancer agent other than anti-MFG-E8 antibody (chemotherapy to MC38 was performed by use of gemcitabine, and to B16 dacarbazine).

The MC38 tumor removed from the mice to which gemcitabine and the anti-MFG-E8 antibody had been administered was found to have increased caspase 3 activity, as compared with the MC38 tumor removed from the mice which had been treated with gemcitabine alone or the anti-MFG-E8 antibody alone (FIG. 15). Similarly, caspase 3 activity in B16 melanoma significantly increased when dacarbazine and the anti-MFG-E8 antibody were used in combination (FIG. 15).

Example 9

Anti-MFG-E8 Antibody and Immunity (Method)

In order to elucidate the relationship between immunity and increased anti-tumor effects of combination therapy using anti-cancer agent and anti-MFG-E8 antibody, tumor cells such as MC38, B16, or MCA-205 were transplanted to immuno-deficient mice and wild-type mice in a manner similar to that of Example 1.

Specifically, established MC38 tumors (25 mm$^2$) transplanted to NOD-SCID mice were treated with the systemic administration of GEM and anti-MFG-E8 monoclonal antibody. Separately, established MC38 tumors transplanted to wild-type C57B1/6 mice from which CD4$^+$ or CD8$^+$, or NK1.1$^-$ cells had been depleted. GEM and an anti-MFG-E8 monoclonal antibody were systemically administered to these wild-type mice. Yet separately, MC38 cells were transplanted to wild-type C57B1/6 mice, and GEM and an anti-MFG-E8 monoclonal antibody were administered to the mice, to thereby suppress growth of MC38 tumors. Fifty days after such successful treatment for the initial tumor challenge, MC38, B16, or MCA-205 was transplanted to these mice, and anti-tumor effects were investigated.
(Results)

Figure 16:
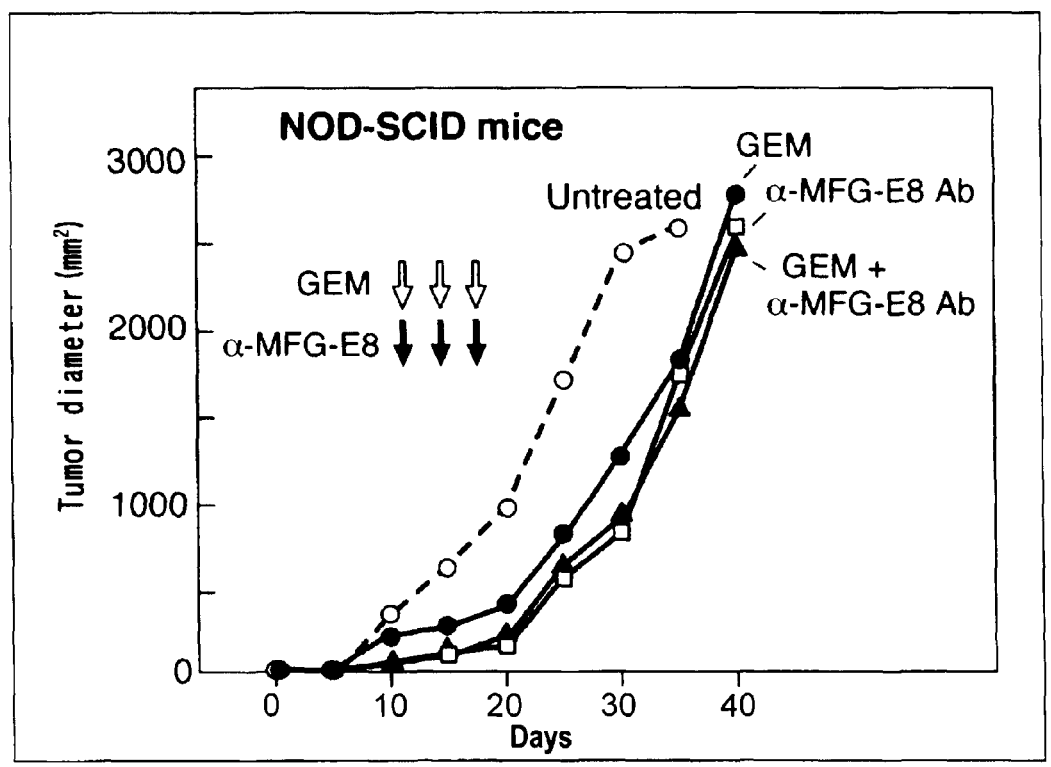
[FIG. 16] A graph showing the effect of combinatory use of anti-MFG-E8 antibody and an anti-cancer agent other than anti-MFG-E8 antibody on subcutaneous tumor models (NOD-SCID mice, mouse colon carcinoma cells (MC38)).
Figure 17:
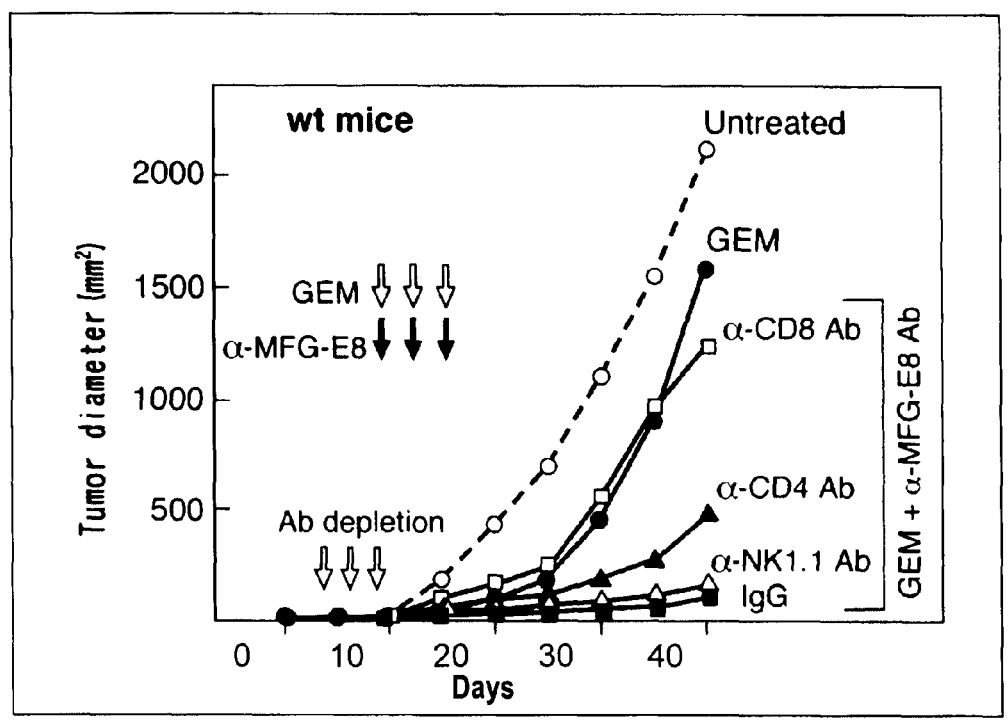
[FIG. 17] A graph showing the effect of combinatory use of anti-MFG-E8 antibody and an anti-cancer agent other than anti-MFG-E8 antibody on mouse colon carcinoma cells (MC38) of wild-type mice in which CD4, CD8, and NK1.1 were inhibited by an antibody.
Figure 18:
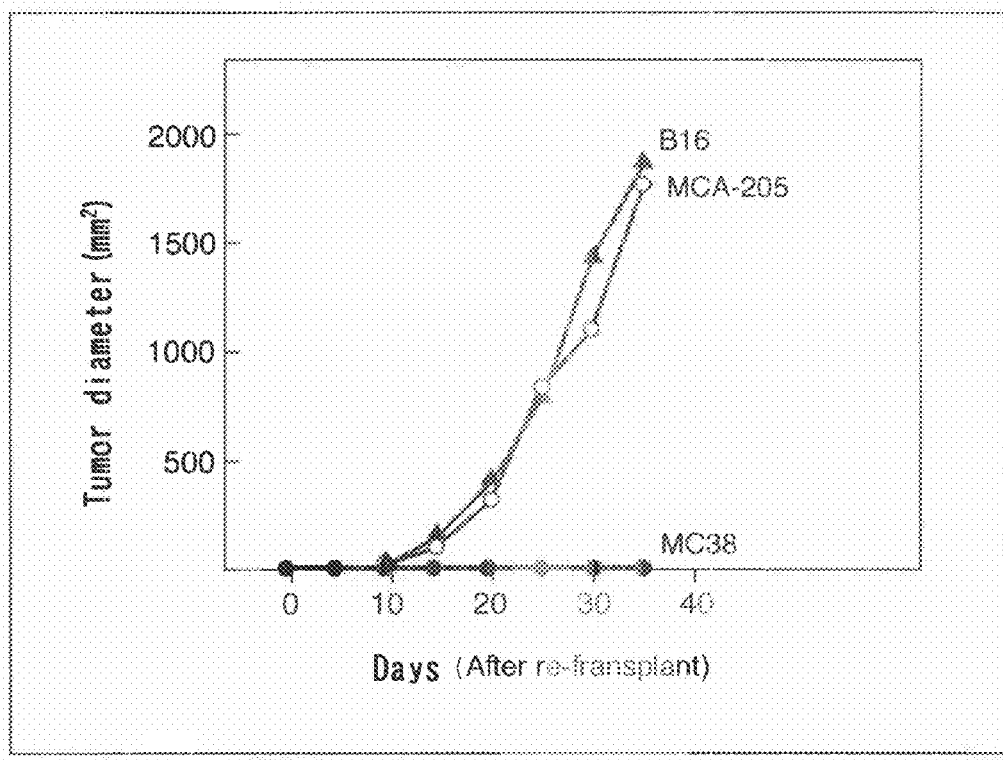
[FIG. 18] A graph showing the action of combinatory use of anti-MFG-E8 antibody and an anti-cancer agent other than anti-MFG-E8 antibody on re-transplant of MC38.

In the NOD-SCID mice, which are immuno-deficient, the effects of the anti-MFG-E8 antibody on potentiation of the anti-tumor effect by the anti-cancer agent which had been observed in Example 1 was not observed (FIG. 16). When CD4$^+$ or CD8$^+$ T cells were depleted with the antibody administration in wild-type mice, the benefit of the combination therapy with anti-cancer agent and anti-MFG-E8 antibody was reduced (FIG. 17). When MC 38 tumor was inoculated again to the mice which had been successfully treated for MC 38 tumor with GEM and the anti-MFG-E8 antibody 50 days before, the growth of MC 38 was still inhibited (FIG. 18). In contrast, no growth inhibitory effect was observed with respect to B16 and MCA-205 which had been transplanted 50 days after the initial treatment for MC 38 (FIG. 18).

Thus, it was further clarified that the potentiation effects on anti-tumor activity of combinatory therapy employing the anti-MFG-E8 antibody and the anti-cancer agent is long-lasting and mediated by the host immune response with high specificity.

Example 10

(Method)

Tumor-infiltrating cells were collected from treated mice, and expression of CD11c, CD11b, and CD86 in the collected cells was examined with flow cytometry. Separately, bone-marrow-derived dendritic cells and PKH26-labeled EG.7-OVA cells (with or without opsonization by anti-MFG-E8 monoclonal antibody) were co-cultivated, and phagocytosis was evaluated.
(Results)

Figure 19:
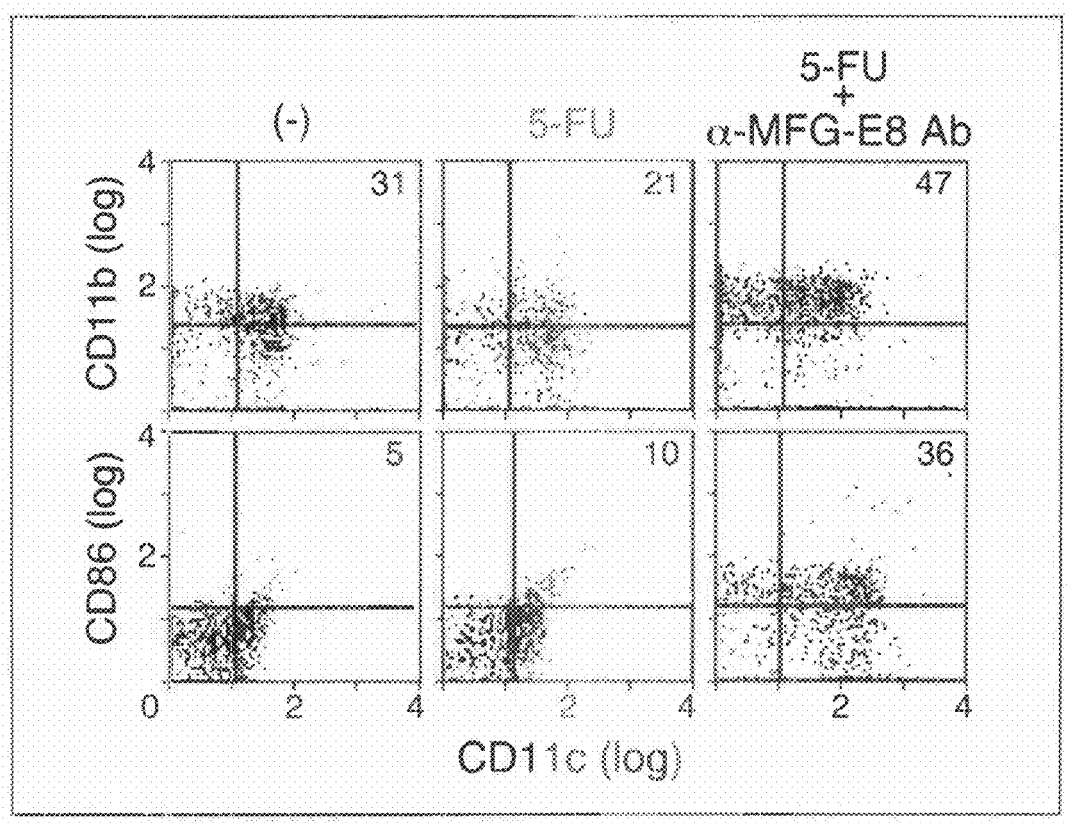
[FIG. 19] Graphs showing the effects on expression of CD11b and CD86, when anti-cancer agent (other than anti-MFG-E8 antibody) and anti-MFG-E8 antibody were administered to the same tumor models as shown in FIG. 1.
Figure 20:
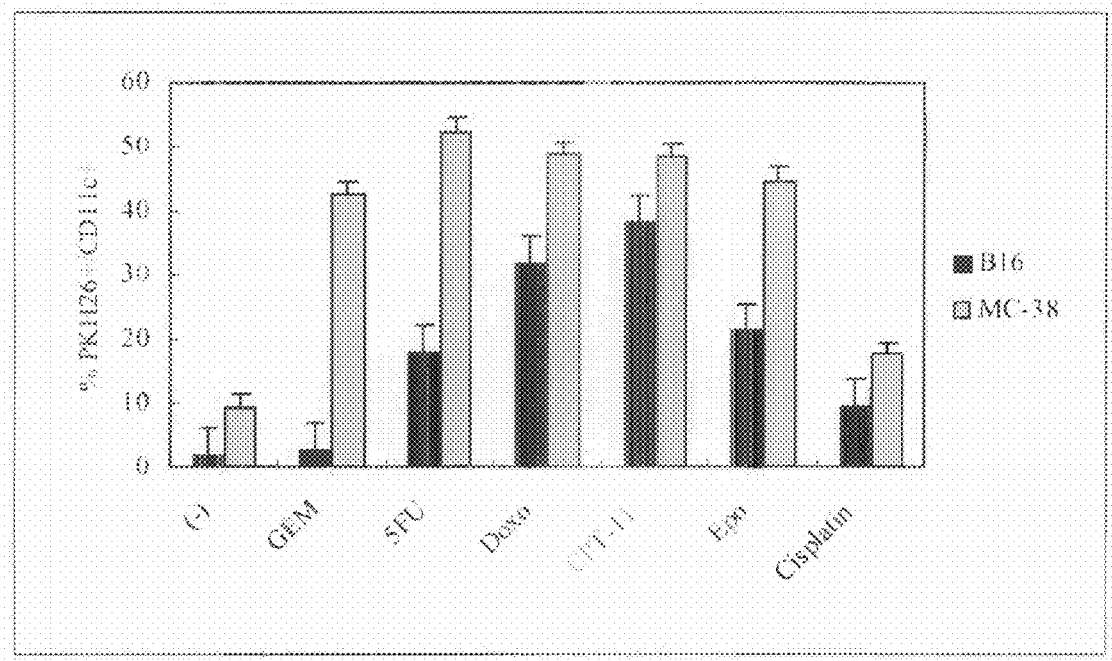
[FIG. 20] A graph showing ingestion of MC38 and B16 cells, when anti-cancer agent (other than anti-MFG-E8 antibody) and anti-MFG-E8 antibody were used.

In the mice treated with combinatory therapy employing the anti-cancer agent and the anti-MFG-E8 antibody, the numbers of CD11b$^+$ and CD11c$^+$ dendritic cells increased significantly. These cells also highly expressed CD86, which relates to co-stimulation (FIG. 19). In an in vitro system, bone marrow-derived dendritic cells effectively ingested chemotherapy-treated MC38 cells and B16 cells (FIG. 20). The analysis on tumor infiltrating cells suggests that in situ capture of tumor cells by dendritic cells may be important for T cell priming.

Example 11

(Method)

Dendritic cells (BMDCs) were prepared through culturing myeloid progenitor cells for seven days in a GM-CSF containing medium, and treated overnight with recombinant MFG-E8 (100 ng/mL, product of R&D Systems), an anti-MFG-E8 monoclonal antibody (20 μg/mL, MBL), or a polyclonal MFG-E8 anti-serum (20 μg/mL). The IL-12, IL-23, TNF-α, and IL-10 concentrations of the culture supernatant were determined with ELISA. On day 7, BMDCs were co-cultured with PKH26 (Sigma-Aldrich)-labeled EG.7-OVA cells using a 12-well plate (ratio: 1:10), and phagocytosis was determined with flow cytometry. A similar experiment was performed using tumor cells treated for 30 minutes with an anti-MFG-E8 monoclonal antibody (30 mg/mL) before the co-culture. The effect of α$_v$β$_3$ integrin-blocking antibody (RMV-7, product of Millipore) or Fc-receptor-blocking antibody (product of BD Bioscience) was also evaluated on the intake of tumor cells. Cross-presentation was tested using the following procedure. Specifically, naive CD4+ T cells were isolated from the spleen of C57BL/6-Tg (ACTB-OVA) 916Jen/J mice using magnetic cell sorting (product of Miltenyi Biotech). The thus-isolated cells were added to the dendritic cells to which tumor cells had been loaded for 24 hours. Expression of IFN-γ within the cells was measured with flow cytometry.

In vivo cross-presentation assay was also performed. Specifically, EG.7-OVA cells ($1 \times 10^6$/mouse) irradiated with an X-ray were administered to the foot pad of OT-I mouse with either MFG-E8 monoclonal antibody (1 mg/mL), anti-FcR-blocking antibody (1 mg/mL), or isotype control. The mouse was sacrificed five days after administration, and lymphoid cells were isolated from the draining lymph nodes. The thus-isolated cells were cultured overnight with MHC class I-restricted OVA peptide (10 mg/mL). Subsequently, by using the culture supernatant, production of IFN-γ by CD8+ T cells was examined with flow cytometry or ELISA.

(Results)

Figure 21:
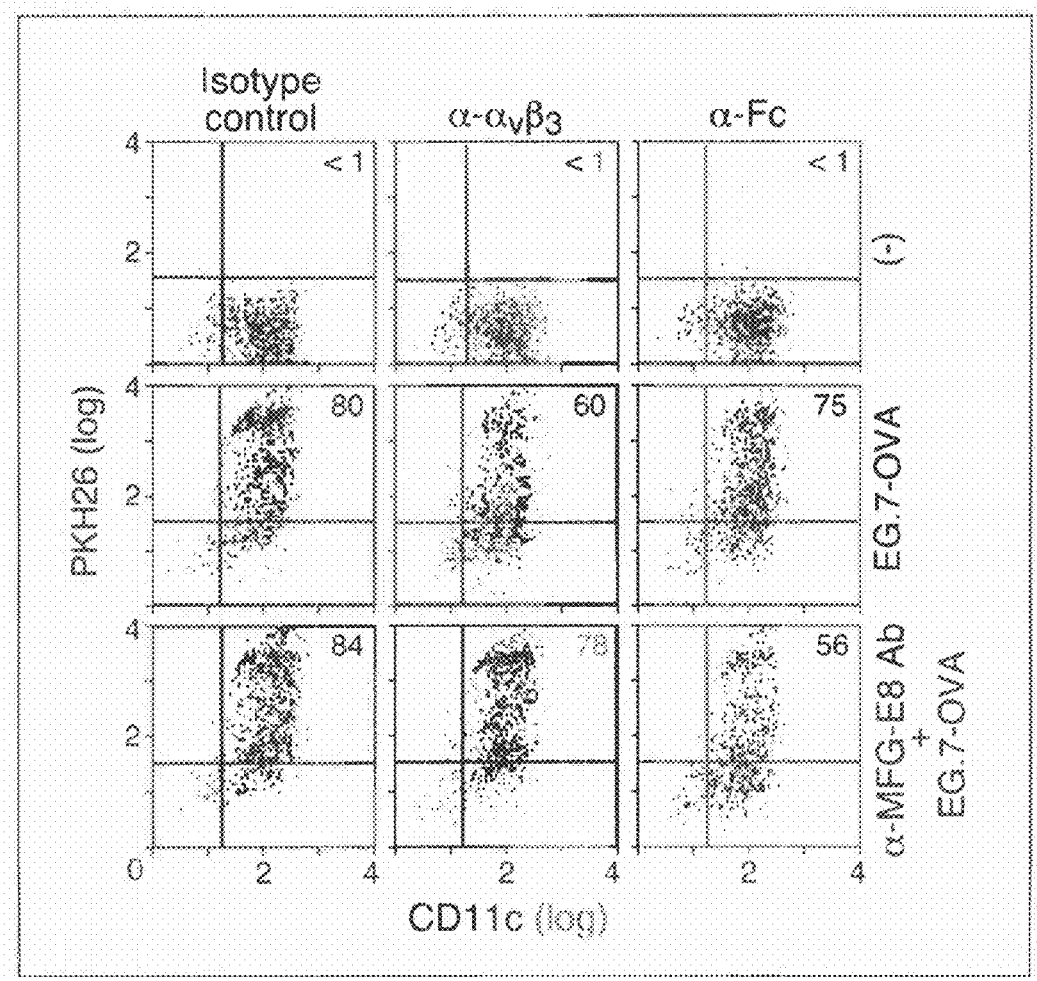
[FIG. 21] A graph showing an increased involvement of Fc receptor with respect to $\alpha_v\beta_3$ integrin by use of anti-MFG-E8 antibody in a test of PKH26-labeled EG7-OVA cell ingestion.

Bone marrow-derived dendritic cells effectively ingested irradiated EG.7-OVA cells. However, the intake was partially inhibited with an antibody to $\alpha_v\beta_3$ integrin. This phenomenon suggests the contribution of MFG-E8 to tumor cell ingestion in the system (FIG. 21). The anti-MFG-E8 antibody did not affect complete ingestion of irradiated EG.7-OVA cells, but an antagonistic antibody not to $\alpha_v\beta_3$ integrin but to an Fc-receptor suppressed intake of EG.7-OVA cells. These phenomena clearly suggest that the anti-MFG-E8 antibody switches the receptors for the ingestion of from $\alpha_v\beta_3$ integrin to an Fc-receptor. Since this switching action is thought to be a characteristic intrinsic function of antibodies which can promote Fc-receptor-mediated intake, the anti-tumor effect associated with the anti-MFG-E8 antibody might be considerably larger than the anti-tumor effect obtained in the case where MFG-E8-blocking agents other than the antibody was used.

Figure 22:
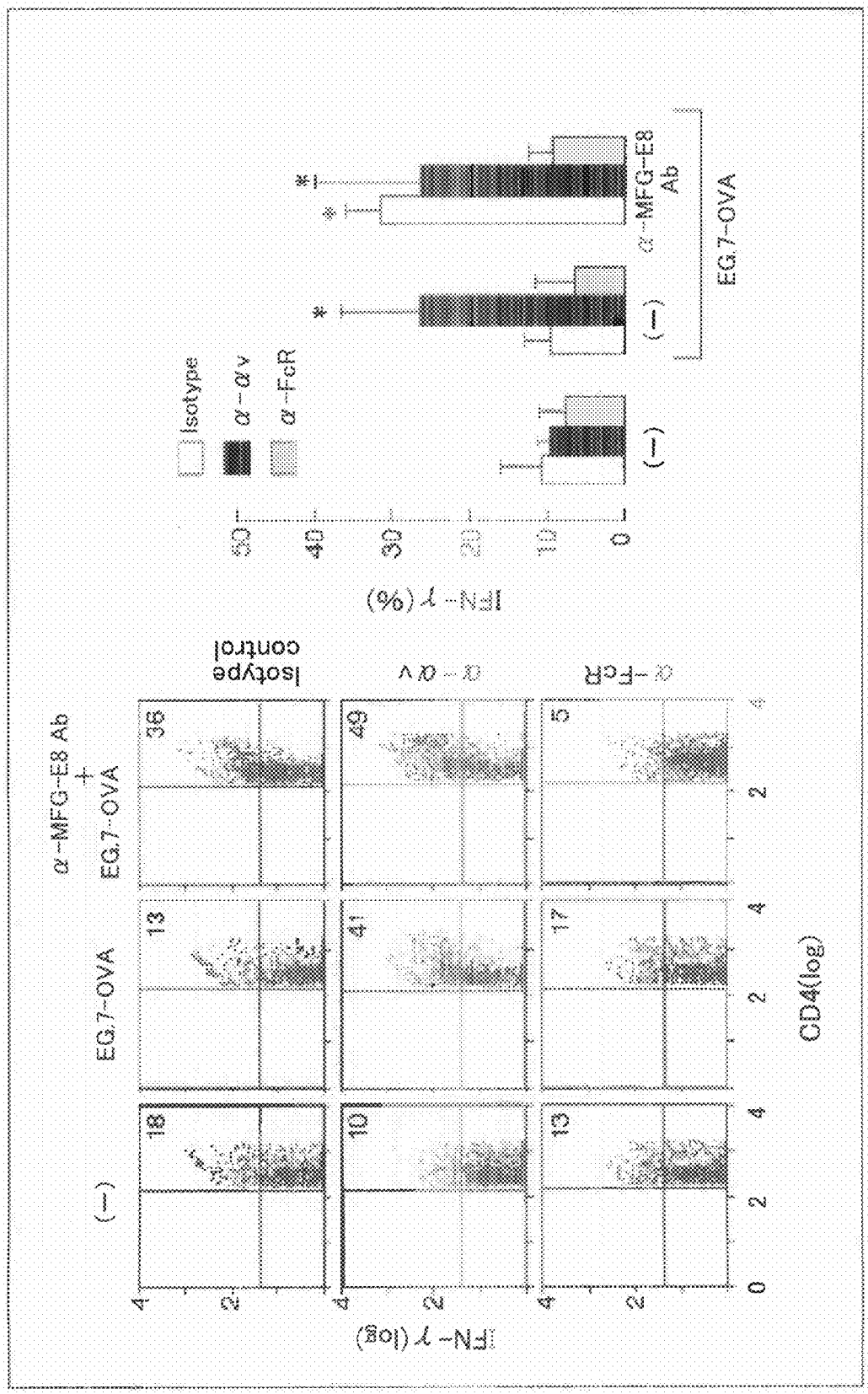
[FIG. 22] Graphs showing the significant involvement of an Fc-receptor-mediated system in the presence of anti-MFG-E8 antibody in cross representation of tumor antigen by dendritic cells (in vitro).
Figure 23:
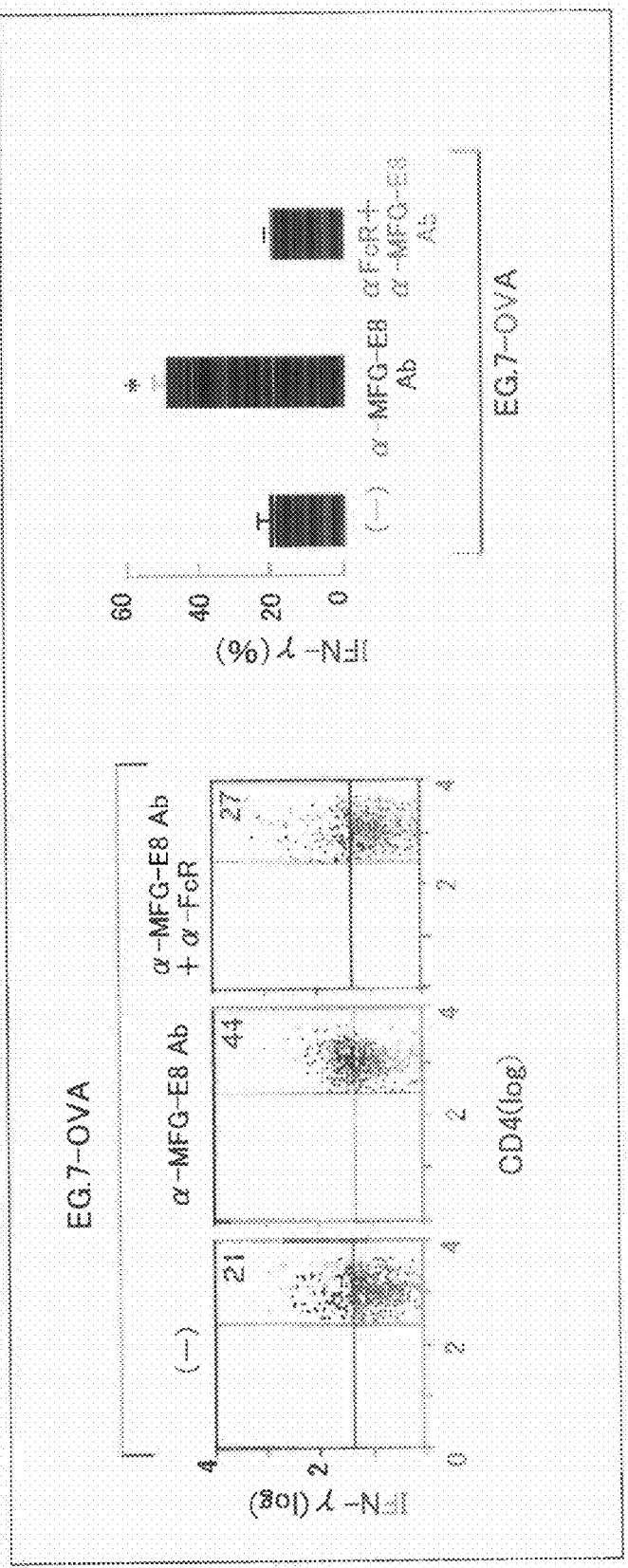
[FIG. 23] Graphs showing the significant involvement of an Fc-receptor-mediated system in the presence of anti-MFG-E8 antibody in cross representation of tumor antigen by dendritic cells (in vivo).

Concomitant with activation of an Fc-receptor inducing immunostimulation, opsonization of EG.7-OVA cells by the anti-MFG-E8 antibody enhanced dendritic-cell-stimulation of OVA TCR transgenic T cells obtained from CS7B1/6 syngeneic mice, resulting in enhancement in IFN-γ production, while the anti-Fc-receptor antibody inhibited cross-priming (FIG. 22, 23). In contrast, the anti-$\alpha_v\beta_3$ integrin antibody enhanced T-cell response of only irradiated EG.7-OVA cells or of EG.7-OVA cells opsonized by the anti-MFG-E8 antibody, thereby transferring irradiated EG.7-OVA cells into dendritic cells. In fact, intake of MFG-E8 through $\alpha_v\beta_3$ integrin present on the surfaces of dendritic cells enhanced secretion of IL-10, while inhibition of intake of MFG-E8 by the anti-MFG-E8 antibody decreased production of IL-10, but increased production of IL-12, IL-23, and TNF-α (FIG. 24). This cytokine profile regulation is thought to contribute to the immune-activation with the anti-MFG-E8 antibody.

Example 12

The influence of the timing of administration of an anti-cancer agent and the anti-MFG-E8 antibody on the anti-tumor effect was investigated. That is, although in Example 1 the anti-cancer agent and the anti-MFG-E8 antibody were administered concomitantly, the timing of administration was modified, whereby the effect of the anti-MFG-E8 antibody on the anti-tumor effect provided together with the anti-cancer agent was investigated.

As a result, through administration of the anti-cancer agent and the anti-MFG-E8 antibody concomitantly, or administration of the anti-cancer agent and subsequently the anti-MFG-E8 antibody, a remarkably more potent anti-tumor effect was resulted. Therefore, it has been clarified that the action of the anti-MFG-E8 antibody is attributed to the activation of the immunogenicity of the tumor cells which have been given cytotoxic effects by the anti-cancer agent.

Example 13

Combinatory Use with Two or More Other Anti-cancer Agents (Method)

The MC 38 mouse colon carcinoma cells ($1 \times 10^5$/mouse) were subcutaneously inoculated. From ten days after the inoculation (tumor diameter: 25 mm²), the following agents were intraperitoneally administered on days 10, 12, 14, 16, and 18.

Chemotherapy alone group: 5FU (20 mg/kg)+CPT-11 (2 mg/mL)

Anti-MFG-E8 antibody alone

Combinatory group: 5-FU (20 mg/kg)+CPT-11 (2 mg/mL)+anti-MFG-E8 blocking antibody (1 mg/kg)

(Results)

In the chemotherapy alone group and the combinatory group, a tumor shrinking effect was observed, and the tumor disappeared on day 30. However, after elapse of a long time (day 120 or after), a clear difference in anti-tumor effect between the two groups was observed. That is, many cases of rapid tumor recurrence were observed in the chemotherapy alone group, but no recurrence was observed in the anti-cancer agent+anti-MFG-E8 antibody combinatory group. Thus, combinatory use of the anti-cancer agent and the anti-MFG-E8 antibody was found to exhibit a long-term tumor-growth inhibitory effect.

The invention claimed is:

1. A method for treatment of cancer, comprising administering, to a patient in need thereof, an anti-MFG-E8 antibody and an anti-cancer agent other than the antibody, in combination, wherein
said treatment is in the absence of administration of a tumor antigen or tumor cell,
the anti-cancer agent is a tumor-cell-toxic anti-cancer agent, and
the anti-MFG-E8 antibody and the tumor-cell-toxic anti-cancer agent are administered separately, and
the anti-MFG-E8 antibody induces an immune response by binding to MFG-E8 to thereby inhibit the function of MFG-E8.

2. The method according to claim 1, wherein the anti-cancer agent is an alkylating agent, a metabolic antagonist, a microtubule inhibitor, an antibiotic anti-cancer agent, a topoisomerase inhibitor, a platinum drug, or a molecular targeted drug.

3. The method according to claim 1, wherein the anti-cancer agent is gemcitabine, 5-FU, CPT-11, etoposide, cisplatin, oxaliplatin, paclitaxel, docetaxel, dacarbazine, doxorubicin, bevacizumab, cetuximab, an anti-vascular endothelial growth factor receptor 2 inhibition antibody, or an epidermal growth factor tyrosine kinase inhibitor.

4. A method for treatment of cancer, comprising administering an anti-MFG-E8 antibody to a patient in need thereof, and a cancer therapy that does not employ the antibody, in combination, wherein said treatment is in the absence of administration of a tumor antigen or tumor cell, wherein the anti-MFG-E8 antibody induces an immune response by binding to MFG-E8 to thereby inhibit the function of MFG-E8.

5. The method of claim 4, wherein the cancer therapy is a cellular therapy.

6. The method of claim 4, wherein the cancer therapy is selected from the group consisting of radiotherapy, MR-guided focused ultrasound surgery, cryotherapy, radio frequency ablation, ethanol-injection and artery embolization, without use of a tumor antigen.

7. The method of claim 4, wherein said method is for treatment of epithelial cancer.

8. The method of claim 7, wherein said epithelial cancer is selected from the group consisting of pharyngeal cancer, laryngeal cancer, tongue cancer, lung cancer, breast cancer, esophageal cancer, stomach cancer, colon cancer, uterus cancer, ovarian cancer, liver cancer, pancreatic cancer, gallbladder cancer, kidney cancer, prostate cancer, malignant melanoma, and thyroid gland cancer.

9. The method according to claim 1, wherein the anti-MFG E8 antibody effectively potentiates the effect of the anti-cancer agent.

\* \* \* \* \*